United States Patent
Stamp

(10) Patent No.: US 8,647,299 B2
(45) Date of Patent: Feb. 11, 2014

(54) AUTOINJECTOR SUPPORTING THE SYRINGE AT THE FRONT

(75) Inventor: Kevin Stamp, Sheffield (GB)

(73) Assignee: The Medical House Limited, Hertfordshire (GB)

( * ) Notice: Subject to any disclaimer, the term of this patent is extended or adjusted under 35 U.S.C. 154(b) by 396 days.

(21) Appl. No.: 12/161,776

(22) PCT Filed: Jan. 17, 2007

(86) PCT No.: PCT/GB2007/000141
§ 371 (c)(1),
(2), (4) Date: Oct. 17, 2008

(87) PCT Pub. No.: WO2007/083115
PCT Pub. Date: Jul. 26, 2007

(65) Prior Publication Data
US 2010/0152655 A1    Jun. 17, 2010

(30) Foreign Application Priority Data

Jan. 23, 2006 (GB) .................. 0601309.8
Feb. 7, 2006 (GB) .................. 0602411.1
Mar. 21, 2006 (GB) .................. 0605644.4
Oct. 12, 2006 (GB) .................. 0620163.6

(51) Int. Cl.
*A61M 5/315* (2006.01)
*A61M 37/00* (2006.01)
*A61M 5/00* (2006.01)

(52) U.S. Cl.
USPC ........... 604/110; 604/131; 604/135; 604/136; 604/157; 604/225

(58) Field of Classification Search
USPC ......... 604/187, 110, 134–138, 156, 157, 263, 604/111, 181, 192–199, 218, 220
See application file for complete search history.

(56) References Cited

U.S. PATENT DOCUMENTS 60,917 A    1/1867  Brown
3,702,608 A  11/1972  Tibbs
(Continued)

FOREIGN PATENT DOCUMENTS

DE  102004060146   8/2005
EP  0 453 212 B1   10/1991
(Continued)

OTHER PUBLICATIONS

Official Action for U.S. Appl. No. 10/767,860, mailed Dec. 2, 2008, 5 pages.
(Continued)

*Primary Examiner* — Theodore Stigell
*Assistant Examiner* — Leah Stohr
(74) *Attorney, Agent, or Firm* — Sheridan Ross P.C.

(57) ABSTRACT

An autoinjector comprising a housing in which can be mounted a syringe comprising a barrel for holding a volume of medicament, a needle at one end of the barrel in fluid communication with the medicament and a plunger axially-moveable in the barrel to a forwardmost position, the autoinjector further comprising a syringe support means for supporting the barrel at an axial location at or forward of the forwardmost position of the plunger and having a reaction surface for the syringe, whereby in use said reaction surface (109) provides an axial compressive force on said barrel when a forward axial force is applied to the plunger.

42 Claims, 22 Drawing Sheets

(56) References Cited

U.S. PATENT DOCUMENTS

| | | | |
|---|---|---|---|
| 3,756,242 A | 9/1973 | Coss | |
| 3,797,489 A | 3/1974 | Sarnoff | |
| 3,811,442 A | 5/1974 | Maroth | |
| 4,617,016 A | 10/1986 | Blomberg | |
| 4,913,699 A | 4/1990 | Parsons | |
| 4,923,447 A | 5/1990 | Morgan | |
| 4,958,622 A | 9/1990 | Selenke | |
| 4,976,724 A | 12/1990 | Nieto et al. | |
| 5,000,744 A | 3/1991 | Hoffman et al. | |
| 5,024,656 A | 6/1991 | Gasaway et al. | |
| 5,042,977 A | 8/1991 | Bechtold et al. | |
| 5,078,698 A | 1/1992 | Stiehl et al. | |
| 5,167,632 A | 12/1992 | Eid et al. | |
| 5,211,625 A | 5/1993 | Sakurai et al. | |
| 5,300,030 A | 4/1994 | Crossman et al. | |
| 5,320,609 A * | 6/1994 | Haber et al. | 604/135 |
| 5,478,316 A | 12/1995 | Bitdinger et al. | |
| 5,599,309 A | 2/1997 | Marshall et al. | |
| 5,634,906 A | 6/1997 | Haber et al. | |
| 5,658,261 A | 8/1997 | Neer et al. | |
| 5,681,291 A | 10/1997 | Galli | |
| 5,779,675 A | 7/1998 | Reilly et al. | |
| 5,779,677 A | 7/1998 | Frezza | |
| 6,203,530 B1 | 3/2001 | Stewart, Sr. | |
| 6,210,369 B1 * | 4/2001 | Wilmot et al. | 604/157 |
| 6,264,629 B1 | 7/2001 | Landau | |
| 6,270,479 B1 | 8/2001 | Bergens et al. | |
| 6,280,421 B1 | 8/2001 | Kirchhofer et al. | |
| 6,544,234 B1 | 4/2003 | Gabriel | |
| 6,620,137 B2 | 9/2003 | Kirchhofer et al. | |
| 6,656,163 B1 | 12/2003 | Marshall et al. | |
| 6,702,608 B2 | 3/2004 | Brennan, Jr. | |
| 6,752,781 B2 | 6/2004 | Landau et al. | |
| 7,118,552 B2 * | 10/2006 | Shaw et al. | 604/110 |
| 7,156,823 B2 | 1/2007 | Landau et al. | |
| 7,976,499 B2 | 7/2011 | Grunhut et al. | |
| 2001/0004681 A1 | 6/2001 | Landau | |
| 2001/0005781 A1 | 6/2001 | Bergens et al. | |
| 2001/0053886 A1 | 12/2001 | Caizza | |
| 2003/0000524 A1 | 1/2003 | Anderson et al. | |
| 2003/0045858 A1 | 3/2003 | Struys et al. | |
| 2003/0093030 A1 | 5/2003 | Landau | |
| 2003/0105430 A1* | 6/2003 | Lavi et al. | 604/136 |
| 2003/0236502 A1 | 12/2003 | De la Serna et al. | |
| 2004/0039336 A1* | 2/2004 | Amark et al. | 604/136 |
| 2005/0027255 A1 | 2/2005 | Lavi et al. | |
| 2005/0165349 A1 | 7/2005 | Stamp | |
| 2005/0165360 A1 | 7/2005 | Stamp | |
| 2006/0100589 A1 | 5/2006 | Lin | |
| 2006/0270984 A1 | 11/2006 | Hommann | |
| 2007/0173770 A1 | 7/2007 | Stamp | |
| 2007/0265568 A1 | 11/2007 | Tsals et al. | |
| 2008/0195056 A1 | 8/2008 | Bishop et al. | |
| 2009/0012471 A1 | 1/2009 | Harrison | |
| 2010/0069846 A1 | 3/2010 | Stamp | |
| 2010/0130930 A1 | 5/2010 | Stamp et al. | |
| 2012/0130342 A1 | 5/2012 | Cleathero | |
| 2012/0136303 A1 | 5/2012 | Cleathero | |

FOREIGN PATENT DOCUMENTS

| | | |
|---|---|---|
| EP | 0 518 416 A | 12/1992 |
| EP | 0740942 | 11/1996 |
| EP | 0864335 | 9/1998 |
| EP | 1 323 447 A2 | 8/2003 |
| EP | 1 323 477 A3 | 8/2003 |
| EP | 2080532 | 7/2009 |
| FR | 2899482 | 10/2007 |
| GB | 886444 | 1/1962 |
| GB | 2443606 | 9/1994 |
| GB | 2388033 A | 11/2003 |
| GB | 2 396 298 A | 6/2004 |
| GB | 2397767 A | 8/2004 |
| GB | 2 410 188 A | 7/2005 |
| GB | 2414398 | 11/2005 |
| WO | WO 94/21316 | 9/1994 |
| WO | WO 99/10030 | 3/1999 |
| WO | WO 99/22792 | 5/1999 |
| WO | WO 0009186 | 2/2000 |
| WO | WO 01/93926 | 12/2001 |
| WO | WO 02/17996 | 3/2002 |
| WO | WO 02/47746 | 6/2002 |
| WO | WO 02/070051 | 9/2002 |
| WO | WO 03/097133 | 11/2003 |
| WO | WO 03/099358 | 12/2003 |
| WO | WO 2004/108194 | 12/2004 |
| WO | WO 2005/009515 | 2/2005 |
| WO | WO 2005/009520 | 2/2005 |
| WO | WO 2005/046765 | 5/2005 |
| WO | WO 2005/070481 | 8/2005 |
| WO | WO 2005/097252 | 10/2005 |
| WO | WO 2005/115507 | 12/2005 |
| WO | WO 2005/115512 | 12/2005 |
| WO | WO 2006/052737 | 5/2006 |
| WO | WO 2006/106291 | 10/2006 |
| WO | WO 2006/106295 | 10/2006 |
| WO | WO 2007/008257 | 1/2007 |
| WO | WO 2007/036676 | 4/2007 |
| WO | WO 2007/083115 | 7/2007 |
| WO | WO 2007/132353 | 11/2007 |
| WO | WO 2006/111862 | 5/2008 |
| WO | WO 2008/075033 | 6/2008 |
| WO | WO 2008/107670 | 9/2008 |
| WO | WO 2008/113864 | 9/2008 |
| WO | WO 2010/026414 | 3/2010 |

OTHER PUBLICATIONS

Interview Summary for U.S. Appl. No. 10/767,860, mailed Feb. 2, 2009, 4 pages.
Official Action for U.S. Appl. No. 10/597,379, mailed Feb. 23, 2009, 9 pages.
U.S. Appl. No. 10/597,379, filed Jul. 21, 2006, Stamp.
Corrected Search Report under Section 17, GB0620163.6, Nov. 24, 2006, Mr. Jeremy Cowen, 1 page.
Office Action for U.S. Appl. No. 10/767,859, mailed Dec. 28, 2007, 7 pages.
Office Action for U.S. Appl. No. 10/767,860, mailed Jan. 11, 2008, 7 pages.
Official Action for U.S. Appl. No. 10/767,860, mailed Dec. 15, 2006, 3 pages.
International Search Report prepared by the European Patent Office on Apr. 27, 2007 for PCT/GB2007/000141; Applicant, Intelligent Orthopaedics Ltd.
Office Action for U.S. Appl. No. 10/767,859, mailed Feb. 24, 2006, 7 pages.
Office Action for U.S. Appl. No. 10/767,859, mailed Jun. 5, 2007, 7 pages.
Office Action for U.S. Appl. No. 10/767,859, mailed Sep. 12, 2006, 9 pages.
Office Action for U.S. Appl. No. 10/767,860, mailed Apr. 10, 2007, 6 pages.
Office Action for U.S. Appl. No. 10/767,860, mailed Aug. 22, 2006, 7 pages.
Office Action for U.S. Appl. No. 10/767,860, mailed Mar. 14, 2006, 7 pages.
Office Action for U.S. Appl. No. 10/767,860, mailed Sep. 24, 2007, 8 pages.
PCT Preliminary Report on Patentability corresponding to International Application No. PCT/GB2005/000223, Jan. 23, 2006, 13 pages.
PCT Written Opinion of the International Searching Authority corresponding to International Application No. PCT/GB2005/000223, Jun. 22, 2005, 7 pages.
Official Action for U.S. Appl. No. 10/767,860, mailed Mar. 14, 2006, 6 pages.
Official Action for U.S. Appl. No. 10/767,860, mailed Jun. 12, 2008, 4 pages.

(56) References Cited

OTHER PUBLICATIONS

Restriction Requirement for U.S. Appl. No. 11/387,645, mailed May 28, 2009, 7 pages.
Official Action for U.S. Appl. No. 11/387,645, mailed Aug. 25, 2010, 16 pages.
Written Opinon for International (PCT) Patent Application No. PCT/GB2007/000141, mailed May 5, 2007, pp. 1-7.
Authorized Officer Mulhausen, International Preliminary Report on Patentability for International (PCT) Patent Application No. PCT/GB2007/000141, dated Jul. 29, 2008.
UK Search Report for Application No. GB0620163.6, dated Nov. 24, 2006, 1 page.
UK Search Report for Application No. GB0602411.1, Apr. 6, 2006.
Advisiory Action for U.S. Appl. No. 10/767,860, mailed Sep. 5, 2008, 3 pages.
Official Action for U.S. Appl. No. 10/597,379, mailed Jul. 31, 2008, 12 pages.
Official Action for U.S. Appl. No. 11/387,645, mailed Sep. 17, 2010, 29 pages.
Formalities Officer Sulis, Communication pursuant to Rule 114(2) EPC for European Patent Application No. 07704923.4, mailed Sep. 29, 2010, 9 pages.
U.S. Appl. No. 12/601,220, filed Nov. 20, 2009, Stamp et al.
U.S. Appl. No. 13/140,483, filed Jun. 17, 2011, Cleathero.
U.S. Appl. No. 13/189,286, filed Jul. 22, 2011, Stamp et al.
Authorized Officer Reinbold, International Search Report issued by the European Patent Office on Mar. 19, 2008 for International Application No. PCT/GB2007/004870, 3 pages.
Authorized Officer Reinbold, Written Opinion issued by the European Patent Office on Mar. 19, 2008 for International Application No. PCT/GB2007/004870, 7 pages.
Authorized Officer Mulhausen, International Preliminary Report on Patentability issued on Jun. 24, 2009 for International Application No. PCT/GB2007/004870, 8 pages.
Authorized Officer Guidoin, International Search Report for International (PCT) Application No. PCT/GB2008/000741, mailed Dec. 23, 2008, 8 pages.
Authorized Officer Urack, Written Opinion for International (PCT) Patent Application No. PCT/GB2008/00741, mailed Dec. 23, 2008, 15 pages.
Authorized Officer Mulhausen, International Preliminary Report on Patentability for International (PCT) Application No. PCT/GB2008/000741, mailed Sep. 17, 2009, 13 pages.
UK Search Report for Application No. GB0804021.4, dated Jul. 1, 2008, 4 pages.
UK Search Report for Application No. GB0704351.6, dated Jun. 7, 2007, 4 pages.
Communication pursuant to Article 94(3) EPC for European Patent Application No. 07704923.7, dated Aug. 2, 2011, 7 pages.

Authorized Officer Bjorklund, International Search Report issued by the European Patent Office for International (PCT) Application No. PCT/GB2009/051716, mailed May 19, 2010, 5 pages.
Authorized Officer Mulhausen, International Preliminary Report on Patentability for International (PCT) Application No. PCT/GB2009/051716, mailed Jun. 23, 2011, 9 pages.
Notice of Allowance for U.S. Appl. No. 10/767,860, mailed Aug. 27, 2009, 8 pages.
Official Action for U.S. Appl. No. 11/387,645, mailed Feb. 11, 2011, 29 pages.
Official Action for U.S. Appl. No. 11/387,645, mailed Jul. 14, 2011, 19 pages.
Notice of Allowance for U.S. Appl. No. 10/597,379, mailed Sep. 2, 2009, 11 pages.
Official Action for U.S. Appl. No. 12/530,107, mailed Apr. 14, 2011, 10 pages.
Official Action for U.S. Appl. No. 12/530,107, mailed Aug. 14, 2011, 9 pages.
"relaxed." Merriam-Webster Dictionary, found on-line at http://www.merriam-webster.com/dictionary/relaxed, Dec. 21, 2011.
Notice of Allowance for U.S. Appl. No. 12/530,107, mailed Jan. 25, 2012, 8 pages.
Official Action for U.S. Appl. No. 11/387,645, mailed Dec. 21, 2011, 21 pages.
Official Action for U.S. Appl. No. 13/189,286, mailed Jan. 4, 2012, 9 pages.
Restriction Requirement for U.S. Appl. No. 12/623,960, mailed Jan. 5, 2012, 6 pages.
Official Action for U.S. Appl. No. 12/623,960, mailed Mar. 5, 2012, 11 pages.
Search Report prepared by the United Kingdom Intellectual Property Office on Aug. 26, 2009, for Application No. GB0906973.3, 2 pages.
Authorized Officer Reinbold, International Search Report for International Application No. PCT/GB2010/050161, dated May 17, 2010, 5 pages.
Authorized Officer Reinbold, Written Opinion for International Application No. PCT/GB2010/050161, issued Aug. 5, 2011, 5 pages.
Authorized Officer Mulhausen, International Preliminary Report on Patentability issued on Aug. 9, 2011 for International Application No. PCT/GB2010/050161, 6 pages.
Notice of Allowance for U.S. Appl. No. 13/189,286, mailed Jun. 22, 2012, 6 pages.
Official Action for U.S. Appl. No. 12/601,220 mailed Jun. 27, 2013, 12 pages.
Official Action for U.S. Appl. No. 13/265,801, mailed Jun. 21, 2013, 8 pages.
Official Action for U.S. Appl. No. 13/147,568 mailed Sep. 6, 2013, 10 pages.

\* cited by examiner

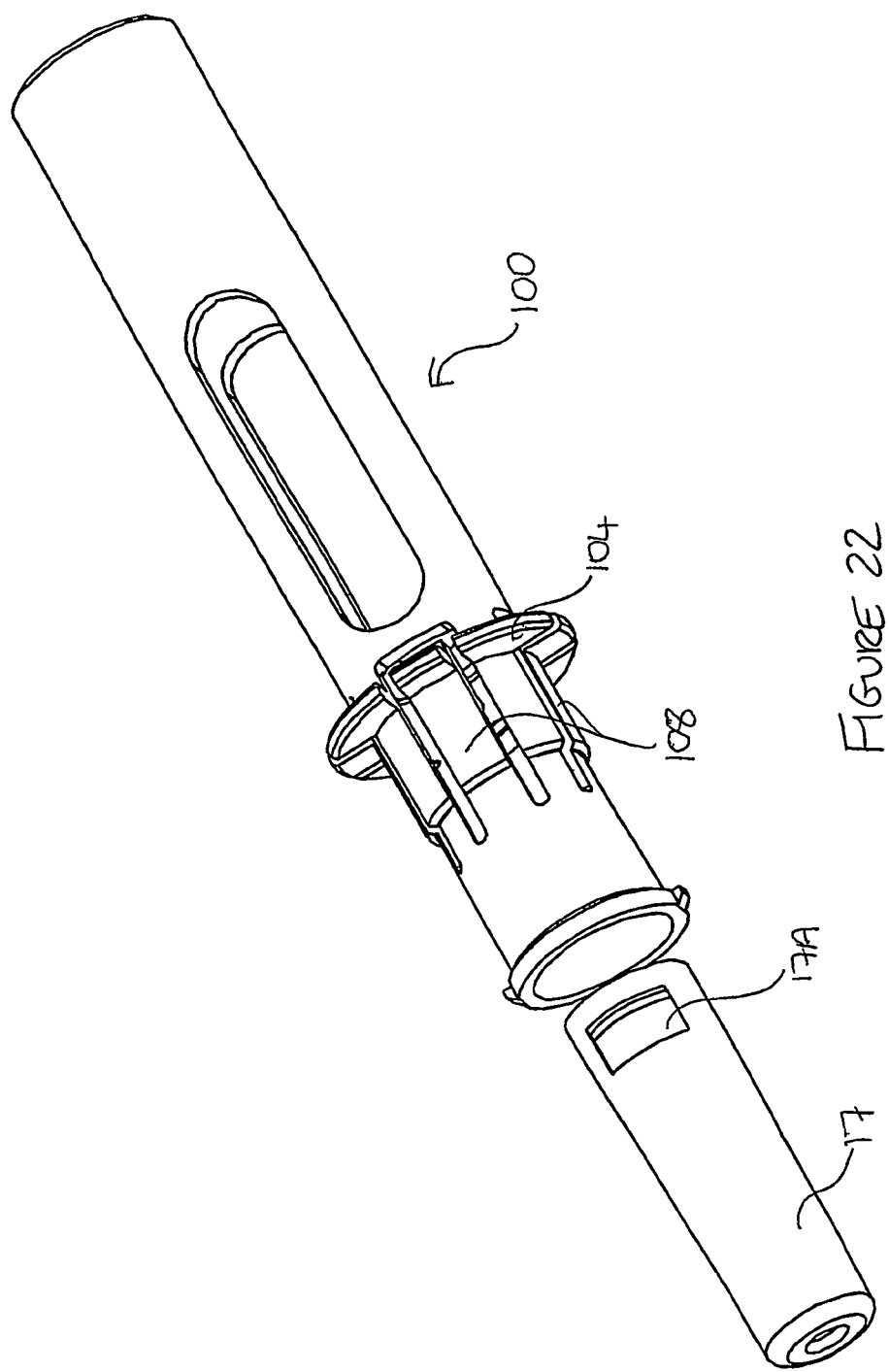

AUTOINJECTOR SUPPORTING THE SYRINGE AT THE FRONT

CROSS REFERENCE TO RELATED APPLICATION

This application is a national stage application under 35 U.S.C. 371 of PCT Application No. PCT/GB2007/000141 having an international filing date of Jan. 17, 2007, which designated the United States, which PCT application claimed the benefit of United Kingdom Application Serial No. 0601309.8, filed Jan. 23, 2006, United Kingdom Application Serial No. 0602411.1, filed Feb. 7, 2006, United Kingdom Application Serial No. 0605644.4, filed Mar. 21, 2006, U.S. application Ser. No. 11/387,645, filed Mar. 22, 2006 and United Kingdom Application Serial No. 0620163.6, filed Oct. 12, 2006, the entire disclosure of each of which is hereby incorporated herein by reference. In addition, this application is a continuation in part of U.S. application Ser. No. 11/387,645, filed Mar. 22, 2006.

This invention relates to the field of autoinjectors for the administration of liquid medication, for example, interferon.

BACKGROUND

An autoinjector is an automatic injection device designed to facilitate automated delivery of a dose of medicament to a patient through a hypodermic needle, the injection usually being administered by the patient themselves. An autoinjector works, for example, by delivering an injection automatically upon actuation by the patient pressing a button, moving a lever or part of a housing etc. This is in contrast to a conventional manual syringe where the patient himself needs to directly depress a plunger into a barrel containing medicament in order to effect the injection. The terms "autoinjector" and "injection device" are used interchangeably in the following description.

Examples of autoinjectors are described in WO2003/099358 (Seedlings Life Science Ventures LLC) and WO01/93926 (Mayo Foundation for Medical Education and Research). These are both generally flat devices which are of small size to encourage users to carry the device with them for ready access. GB2396298 (PA Consulting Services Ltd) is an example of a more conventionally-shaped elongate autoinjector, but of relatively complex internal construction.

All three of the above prior art devices have a custom designed medicament chamber therein rather than being built around a standard pre-filled syringe presentation. The custom medicament chamber, although allowing for a compact overall size for the device, means that the device as whole must be subjected to more rigorous regulatory control as compared with a device containing a standard pre-filled syringe presentation which will have already obtained regulatory approval.

Another reason why the above prior art cannot be used in conjunction with a standard syringe presentation is related to the needle. Usually, a standard pre-filled syringe presentation to be used within a disposable autoinjector includes a needle in communication with a medicament chamber contained within the barrel of the syringe. It is essential that the sterility and integrity of the needle is maintained and protected right up until the moment it is required to deliver an injection. Usually this is achieved by providing a needle sheath comprising a solid (for example an elastomer such as rubber) sheath into which the needle is staked or spiked so that it is surrounded and sealed on all sides. Usually, at least the forwardmost 3-4 mm of the needle is embedded in the rubber of the needle sheath. The autoinjector cannot be operated with the needle sheath in place. Immediately prior to actuating the device, the user removes the needle sheath, for example by removing an endcap from the device to which the needle sheath is attached, so that the needle is ready for use. In contrast, WO01/93926 for example has an entirely different type of needle sheath 79 which is designed to be ruptured by the forward-moving needle during use of the autoinjector. In other words, this type of rupturable needle sheath does not need to be removed from the device before actuation, however, such needle sheaths are likely to provide less mechanical protection than those provided in a standard pre-filled syringe presentation and usually do not directly maintain sterility of the medicament and the needle.

In general, an autoinjector includes a needle which is located within the housing of the device. Upon activation of a force-generating source, a portion of the needle extends out of the housing and penetrates the outer layer of skin to deliver medicament. In some known autoinjectors, after activation, a needle cover or needle shield moves forward to conceal the needle after use. In GB2396298, the needle automatically retracts back into the housing by means of a biasing spring.

An improved autoinjector is described in our co-pending international patent application, published under number WO 2005/070481. Some of the reference numerals in the present application correspond with the equivalent components in the device described in WO 2005/070481. This device requires that the needle is moved axially so that it can appear beyond the end of the nozzle for the duration of the injection, after which the needle retracts automatically, so that it is never in sight of the user. The device also requires that the plunger is moved axially so that medicament is ejected. The overall complexity of the autoinjector is significantly reduced by both of these requirements being effected by one component, namely an inner housing and the device has the significant advantage that it can be built around a conventional or standard syringe presentation.

The injection device of WO 2005/070481 is designed to be used in conjunction with a standard drug presentation e.g. a pre-filled syringe comprising a needle, barrel pre-filled with medicament and a plunger. The plunger may include a separately-provided plunger rod. As mentioned above, there is a significant commercial advantage in being able to use a standard pre-filled syringe, which will have been subjected to numerous clinical trials, drug stability studies and regulatory approval. Any modification to the standard syringe may require further trials and approval, adding delay and expense. The present invention is relevant to any injection device for use in conjunction with a standard pre-filled syringe presentation (whether preloaded or not and whether single-use or reusable), not only the device described in WO 2005/070481.

The barrel of a syringe is usually glass, since glass has the most favourable storage properties for many drugs. However, glass is notoriously fragile and there is a risk of damage or breakage of the syringe during injection if the forces to which the syringe is subjected by the injection device are not properly controlled. This is particularly so where the liquid medicament is relatively viscous, requiring greater force to expel it from the syringe via the needle. Barrels made of materials other than glass, for example polyethylene or cyclic olefin polymers are less brittle when subjected to normal forces during injection, but still would benefit from the invention described below.

In the known device described in our co-pending patent application no WO 2005/070481 and illustrated in FIGS. 1-3 of the present application, the syringe is supported within the injection device by a barrel or syringe holder 9. The syringe holder 9 comprises an elongate housing which closely surrounds the glass barrel of the syringe. The annular flange 90 at the rear of the syringe barrel rests on a barrel seat 91 at the rear of the syringe holder 9. The annular flange 90 at the rear of the syringe barrel is often referred to as a "finger flange" because, during a conventional (manual) injection using a syringe, the user's index and middle fingers rest naturally in front of the "finger flange" in order to provide the necessary resistance to allow depression of the plunger by the thumb to deliver the medicament.

The barrel seat, for example in the form of an annular flange, preferably prevents forward axial movement of the syringe with respect to the syringe holder so that, in use, the syringe barrel and the syringe holder move axially together as one unit.

In use, as described in WO 2005/070481, there are three stages of delivering an injection. Before delivering an injection (referring to FIG. 1 of the present application), the end cap 15 is pulled off, removing the needle cover 17 (if present) and rubber needle sheath 16 with it from the needle. In the first stage of delivering an injection, as shown in FIG. 2 of the present application, the tags 7B at the forward end of the inner housing 7 are in contact with the syringe barrel 90, which is pushed axially forward (taking the syringe holder 9 with it), so that the needle 10, which is fixed to the front end of the barrel, moves in the direction indicated by the arrow so that eventually it protrudes beyond the nozzle 11 at the front of the device. Forward travel of the barrel and syringe holder is limited when a surface 9A of the syringe holder reaches an endstop 11A inside the nozzle or front housing 11.

Referring now to FIG. 3, the second stage of the injection is the delivery of the medicament wherein the tags 7A at the rear of the inner housing 7 depress the plunger 8 into the barrel of the syringe. During this stage, the barrel of the syringe is held axially stationary, by abutment of the annular "finger" flange 90 against the barrel seat 91, which results in the barrel being placed in tension as the plunger pushes the non-compressible liquid medicament towards the forward end of the barrel. This tension is undesirable in a glass barrel, which may become damaged or broken, especially if the medicament comprises a particularly viscous liquid which requires greater force to expel it from the syringe via the needle. Viscous medicaments are desirable in certain applications, where the use of a sustained-release viscous medicament reduces the frequency that an injection is required.

It is desirable to minimise the diameter of the needle so far as is possible, because the smaller the diameter of the needle, the less painful is the resulting injection. However, for a given length of needle, the smaller the needle diameter, the greater the force required to eject the medicament from the syringe.

It is also desirable to minimise the duration of the injection, i.e. to maximise the speed at which the medicament is delivered from the syringe. Particularly when the needle diameter is small, minimising the duration of the injection also means an increase in the force used to eject the medicament from the syringe.

An increase in the forces on the syringe consequently increases the likelihood of the syringe breaking during the injection. The risk of the syringe breaking during injection is significant, and is not only inconvenient and costly but is also potentially dangerous. If breakage occurs, it is possible that glass fragments and/or the needle may become detached and exit the front of the device causing injury. Furthermore, there is the risk that the remaining medicament will leak or be ejected from the device in an uncontrolled manner, potentially delivering the wrong dose into the patient, or causing injury e.g. if the medicament contacts the patient's skin or eyes. These problems are amplified when the medicament is viscous as a more powerful energy source is needed in such applications so that the forces involved are greater. It is known that a typical breakage of the syringe during injection would occur at the finger flange, whereby the finger flange 90 on the syringe barrel breaks as a result of its abutment against the barrel seat 91. It is therefore highly desirable to minimise the likelihood of breakage of the syringe.

In the third stage of the injection (not illustrated in the present application but shown in WO 2005/070481), once the medicament has been delivered and the inner housing 7 is no longer in contact with the barrel or plunger of the syringe, the secondary spring 12 pushes the syringe holder (and hence the syringe contained therein) axially rearwardly so as to retract the syringe back into the housing so that the used needle is concealed from view.

SUMMARY OF THE INVENTION

According to a first aspect of the present invention, there is provided an autoinjector comprising a housing in which can be mounted a syringe comprising
  a barrel for holding a volume of medicament,
  a needle at one end of the barrel in fluid communication with the medicament,
  a plunger axially-moveable in the barrel to a forwardmost position, the autoinjector further comprising
  a needle sheath which seals the forwardmost end of the needle to maintain sterility of the medicament within the barrel whereby, in use, the needle sheath must be removed from the needle immediately prior to actuating the autoinjector; and
  a syringe support means for supporting the barrel at an axial location at or forward of the forwardmost position of the plunger and having a reaction surface for the syringe, whereby in use said reaction surface provides an axial compressive force on said barrel when a forward axial force is applied to the plunger.

Preferably, the autoinjector is a single-use autoinjector. The simple construction of the autoinjector makes it very appropriate for applications such as emergency use for injecting a large population to control a pandemic, where a large number of cost-effective disposable autoinjectors are required. A single-use autoinjector also provides a very convenient means for patients to administer their own injections, even if lacking in dexterity and/or clinical experience. Delivery of viscous drugs is particularly problematic for patients lacking dexterity because of the greater force needed to deliver such drugs—this problem being alleviated by the present invention.

Typically, the autoinjector contains an energy source, for example a coiled spring, for moving said plunger axially in the barrel to deliver an injection in less than 30 seconds.

Preferably, the syringe is axially moveable in said housing and is biased so that the needle is normally wholly inside said housing, wherein before injection the syringe is movable axially so as to move at least a part of said needle out of the housing and wherein after injection, the syringe is able to retract in order to retract said part of said needle into the housing. The concealment of the needle both before and after injection makes the autoinjector particularly suitable where the patient has any aversion to injection by needle. Retraction and retention of the needle after injection eliminates the risk of needle-stick injury.

According to a second aspect of the invention there is provided a method of assembling an autoinjector comprising the steps of:

providing a first part-assembly comprising a front housing and a closely fitting end cap;

providing a second part-assembly comprising a rear part of the autoinjector;

providing a syringe comprising a barrel for holding a volume of medicament, a needle at one end of the barrel and a plunger axially-moveable in the barrel to a forwardmost position;

providing a syringe support means;

inserting the syringe axially into the rear end of the syringe support means until said syringe support means supports the syringe;

inserting the front end of said syringe and syringe support means into said first part-assembly;

assembling said first part-assembly and second part-assembly together so that said syringe support means supports the syringe at an axial location at or forward of the forwardmost position of the plunger, whereby in use said reaction surface provides an axial compressive force on said barrel when a forward axial force is applied to the plunger.

According to a third aspect of the invention there is provided a method of assembling an autoinjector comprising the steps of:

providing a first part-assembly comprising a syringe support means, a front housing and a closely fitting end cap;

providing a second part-assembly comprising a rear part of the autoinjector;

providing a syringe comprising a barrel for holding a volume of medicament, a needle at one end of the barrel and a plunger axially-moveable in the barrel to a forwardmost position;

inserting the syringe axially into the rear end of the first part-assembly until said syringe support means supports the syringe;

assembling said first part-assembly and second part-assembly together so that said syringe support means supports the syringe at an axial location at or forward of the forwardmost position of the plunger, whereby in use said reaction surface provides an axial compressive force on said barrel when a forward axial force is applied to the plunger.

Further features of the invention are defined in the appended claims.

BRIEF DESCRIPTION OF THE DRAWINGS

Preferred embodiments of the present invention will now be more particularly described, by way of example only, with reference to the accompanying drawings in which:

FIG. 22 is a perspective view of another embodiment of the syringe holder together with a needle cover.

DETAILED DESCRIPTION

Figure 1:
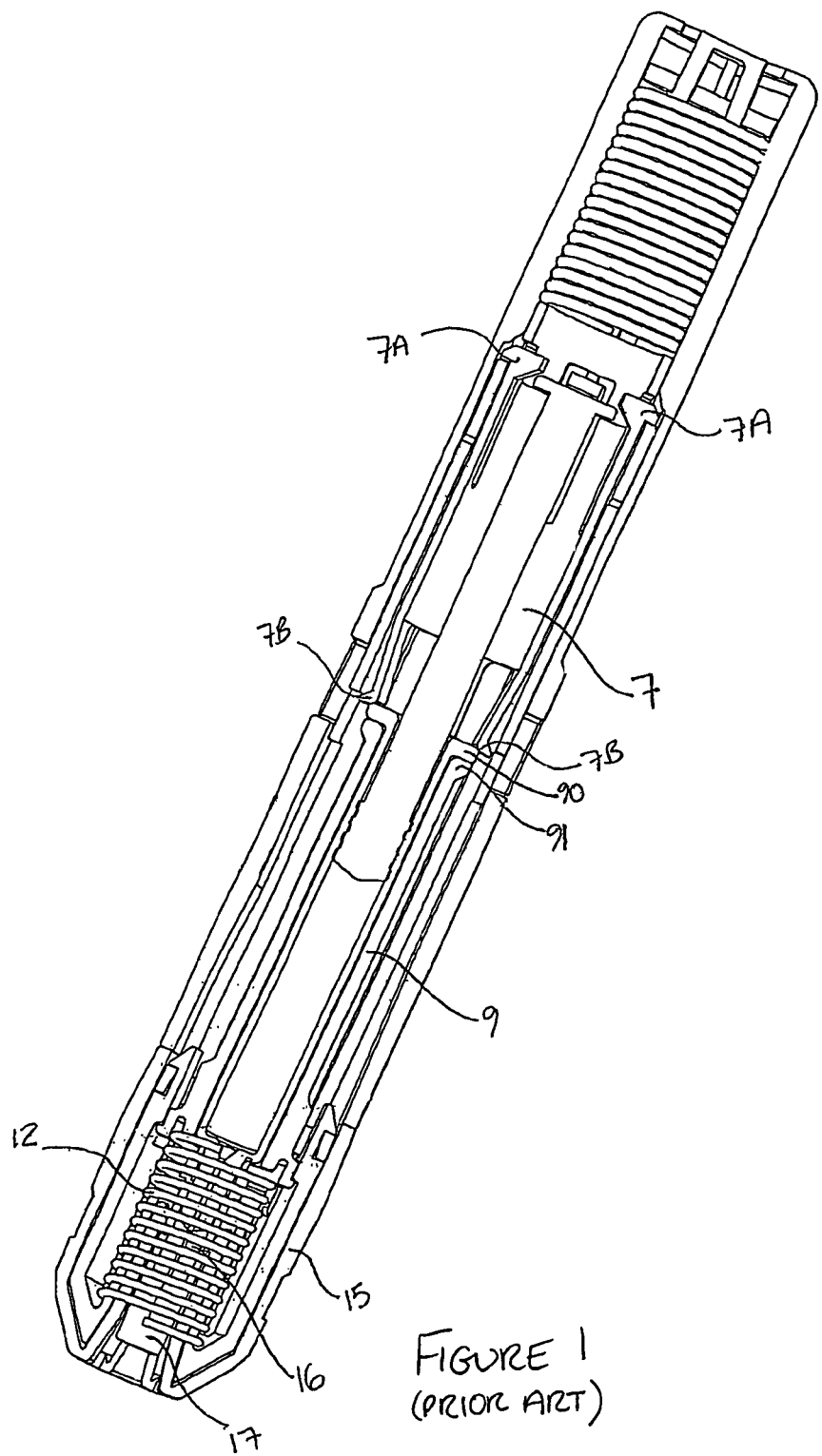
FIG. 1 (PRIOR ART) is a perspective view of a known injection device.
Figure 2:
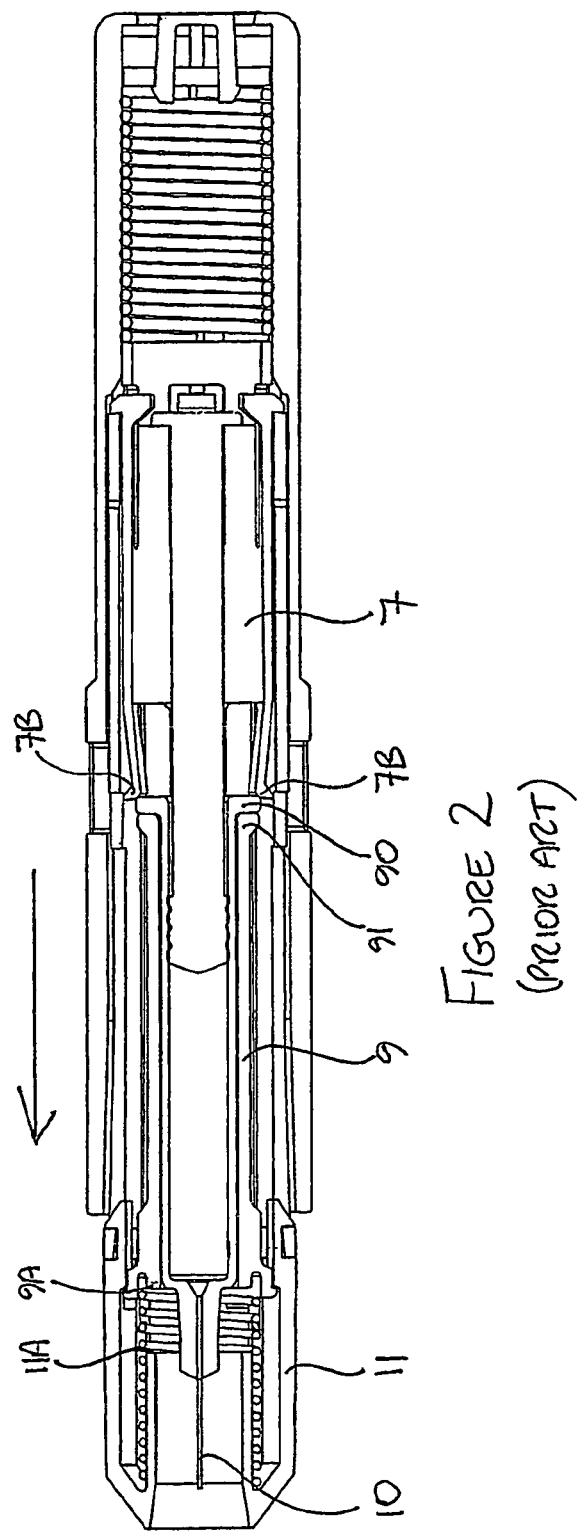
FIG. 2 (PRIOR ART) is a plan view, partly in section of the FIG. 1 device, with the cap and needle cover removed, ready for actuation.
Figure 3:
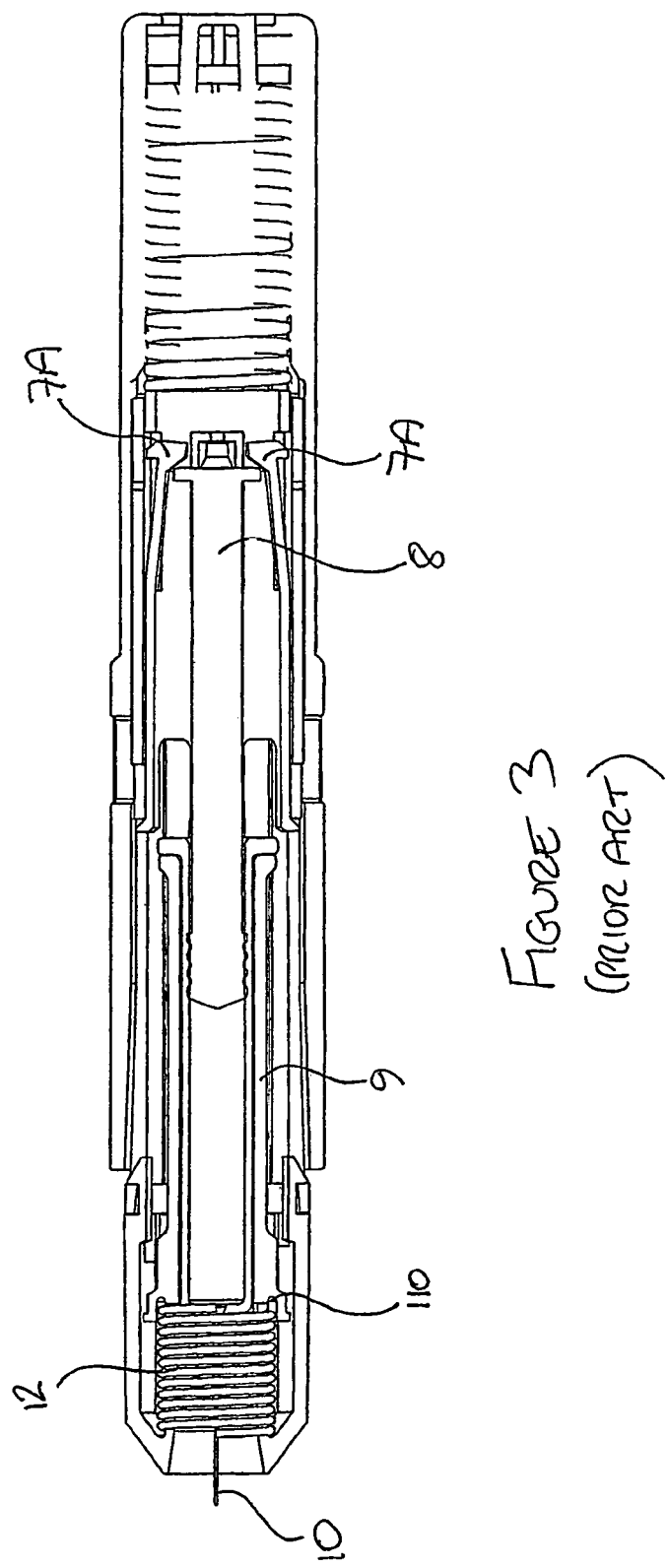
FIG. 3 (PRIOR ART) is a plan view, partly in section of the FIG. 1 device, with the needle exposed, ready for the plunger to be depressed in order to deliver the medicament.

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

The "plunger" includes any elastomeric stopper or the like which seals the chamber containing liquid medicament. The plunger typically also includes a plunger rod but this may be provided separately from the elastomeric stopper and need not be an essential part of the syringe. The "forwardmost position" of the plunger refers to the forwardmost position of any part of the plunger (typically the forwardmost edge of the stopper).

Features, integers, characteristics or groups described in conjunction with a particular aspect, embodiment or example of the invention are to be understood to be applicable to any other aspect, embodiment or example described herein unless incompatible therewith.

As described above, a disadvantage of the known prior art is that the barrel of the syringe is placed in tension as the plunger pushes the non-compressible liquid medicament towards the forward end of the barrel for delivery. This tension is undesirable in a glass barrel, which may become damaged or broken, especially if the medicament comprises a particularly viscous liquid which requires greater force to expel it from the syringe. There is a possibility that the glass syringe might break in the region of its finger flanges, as a result of the forces to which it is subjected during delivery of an injection. One way to mitigate this problem is to reduce the effect of those forces in the region of the finger flanges. For example, the syringe holder of WO 2005/070481 can be modified by providing a helical slit at the rear end thereof which, in use, provides resilience to the region of the barrel seat on which is located the finger flange of the syringe (not illustrated). The resilient flexing absorbs shock and reduces the risk of breakage of the syringe in the region of the finger flanges.

Other means for reducing the effect of forces in the region of the finger flanges can be envisaged, for example, providing a cushion in the form of an O-ring or moulding a relatively soft or elastomeric material into a harder substrate in the region of the barrel seat.

It is known that a typical breakage of the syringe during injection would occur at the finger flange, whereby the finger flange 90 on the syringe barrel breaks as a result of its abutment against the barrel seat 91. However, the applicant has recognised that it is also possible that the syringe could break at points on the barrel forward of the finger flange. This is potentially more serious as larger straight glass fragments may be ejected from the front of the device, as well as the unsecured needle, and any remaining medicament will leak out in an uncontrolled manner.

The risk of breakage or damage to the glass syringe may be reduced by ensuring that the barrel is held in compression during delivery of the medicament (stage two of the injection process described in WO 2005/070481), rather than being in tension. This can be achieved by supporting the forward end of the barrel and having a reaction surface at which an axial compressive force can be applied to the barrel when a forward axial force is applied to the plunger during delivery of the medicament.

Figure 9:
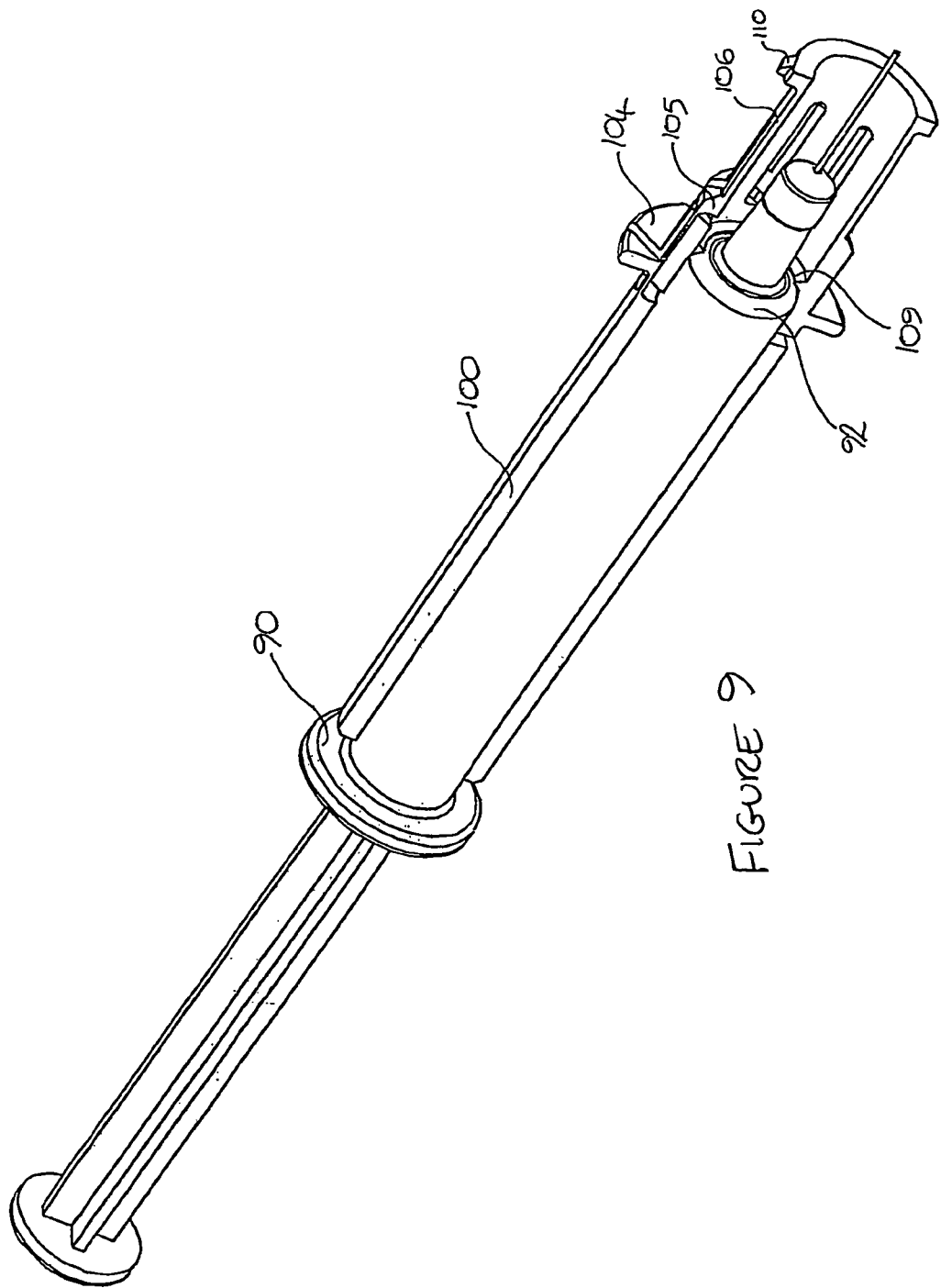
FIG. 9 is a cross-section view of the syringe holder of FIG. 7, showing a syringe in place.

In the injection device of the present invention, the conventional syringe holder 9 is replaced with a more complex syringe holder which is capable of supporting the syringe at the front end of its barrel instead of at its rear flange 90 during delivery of the medicament. In the embodiment described below, the syringe holder supports the syringe at the front shoulder of its barrel and provides a reaction surface there for the front shoulder of the barrel. By "front shoulder" is meant the region at which the largest diameter of the barrel reduces to a smaller diameter at the nozzle. The front shoulder 92 is indicated in FIG. 9. Alternatively, the syringe could be supported and the reaction surface provided at the front end of the syringe barrel, or at the narrowed "cone" where the needle is attached thereto and these embodiments are described in more detail below. The syringe can, in fact, be supported at any place on the barrel which, in use, is forward of the forwardmost position of the fully-depressed syringe plunger and where a reaction surface for the syringe can be provided (so that the barrel is held in compression throughout the delivery of the medicament).

However, the desired supporting or holding of the barrel by the syringe holder at its front end presents an assembly difficulty for a product where it is desired to keep manufacturing and assembly costs to a minimum. In the prior art device, the syringe can simply be dropped into the rear end of the syringe holder until its flange 90 rests on the barrel seat 91. This determines the axial position of the syringe with respect to the syringe holder. In practice, the prior art syringe holder is supplied ready-assembled with the front part of the device, so that the pre-filled syringe can simply be dropped into the syringe holder and then the front part of the device (including the syringe) can be attached to the ready-assembled rear part of the device in a simple two-stage assembly operation.

In the present invention, it is not possible to use the finger flange 90 and barrel seat to determine the axial position of the syringe with respect to the syringe holder. This is because the syringe holder needs to actively support the syringe at its front end (preferably at the front shoulder 92 of the glass barrel). In the preferred embodiment there are inwardly-directed gripping means to retain the front shoulder of the glass barrel at a specific axial location with respect to the syringe holder. The standard syringe is usually supplied with a needle cover 17 which typically has a diameter almost the same as the largest diameter of the glass barrel (see FIG. 10). The needle cover 17 may be rigid, but is not necessarily so. Inside the needle cover 17, the needle is staked or spiked inside a needle sheath 16, which may be made from rubber. If the syringe is inserted into the syringe holder needle-first (or rather needle-cover first), any inwardly-directed gripping means would foul on the needle cover (or needle sheath if no needle cover is present) as they attempt to pass. There is also the risk of the needle being damaged during assembly, for example if it is pushed into any inwardly-directed gripping means. Such damage to the needle is highly undesirable, as it could cause injury to the patient or could affect or impede delivery of medicament, in particular because it often cannot be readily detected if the needle is concealed within a needle cover and/or a rubber needle sheath. The damage to the needle may only become apparent during delivery of the medicament. The consequent effect of a damaged needle on delivery of medicament may not be apparent to the patient at all.

Figure 7:
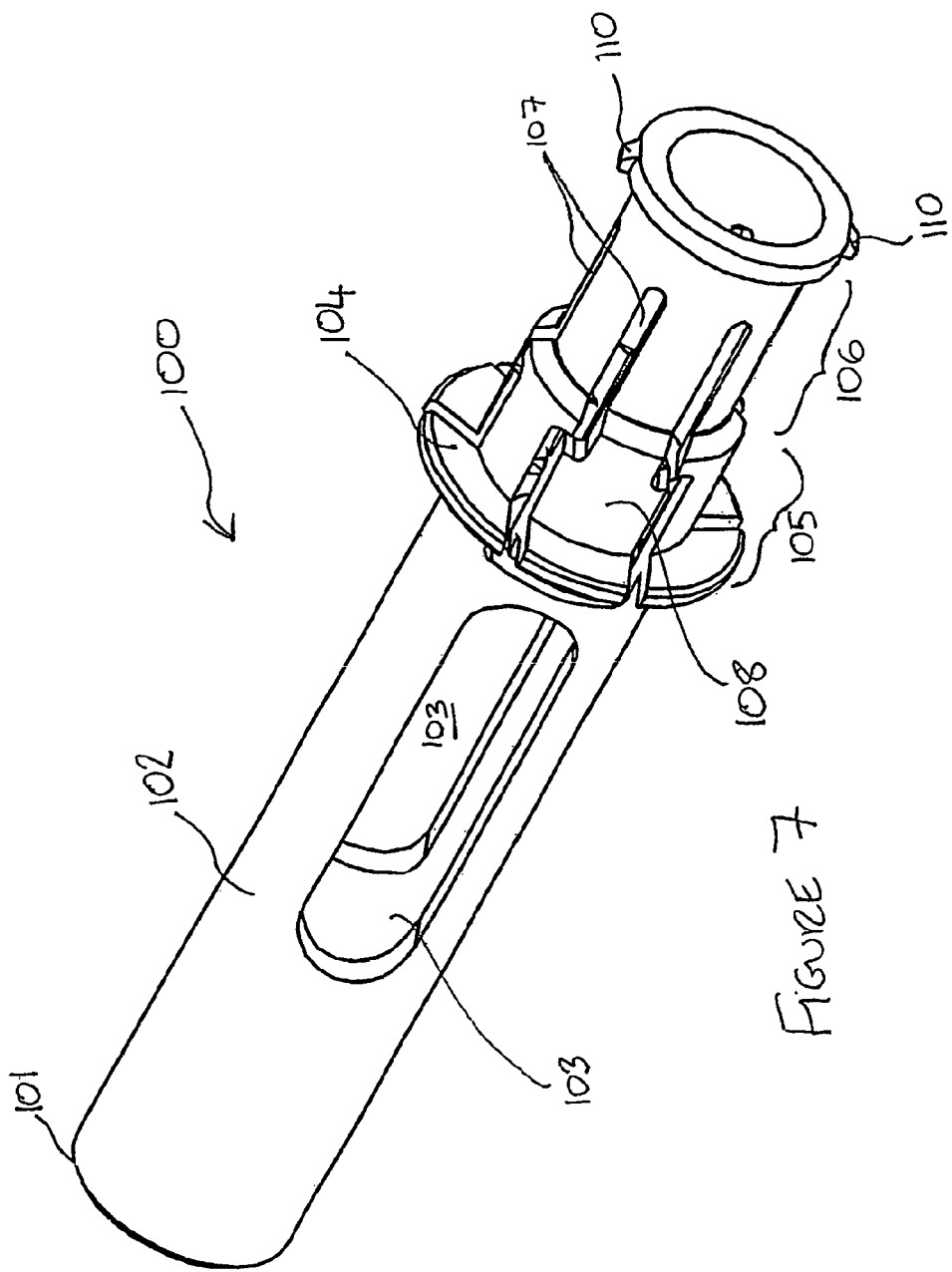
FIG. 7 is a perspective view of the syringe holder.
Figure 8:
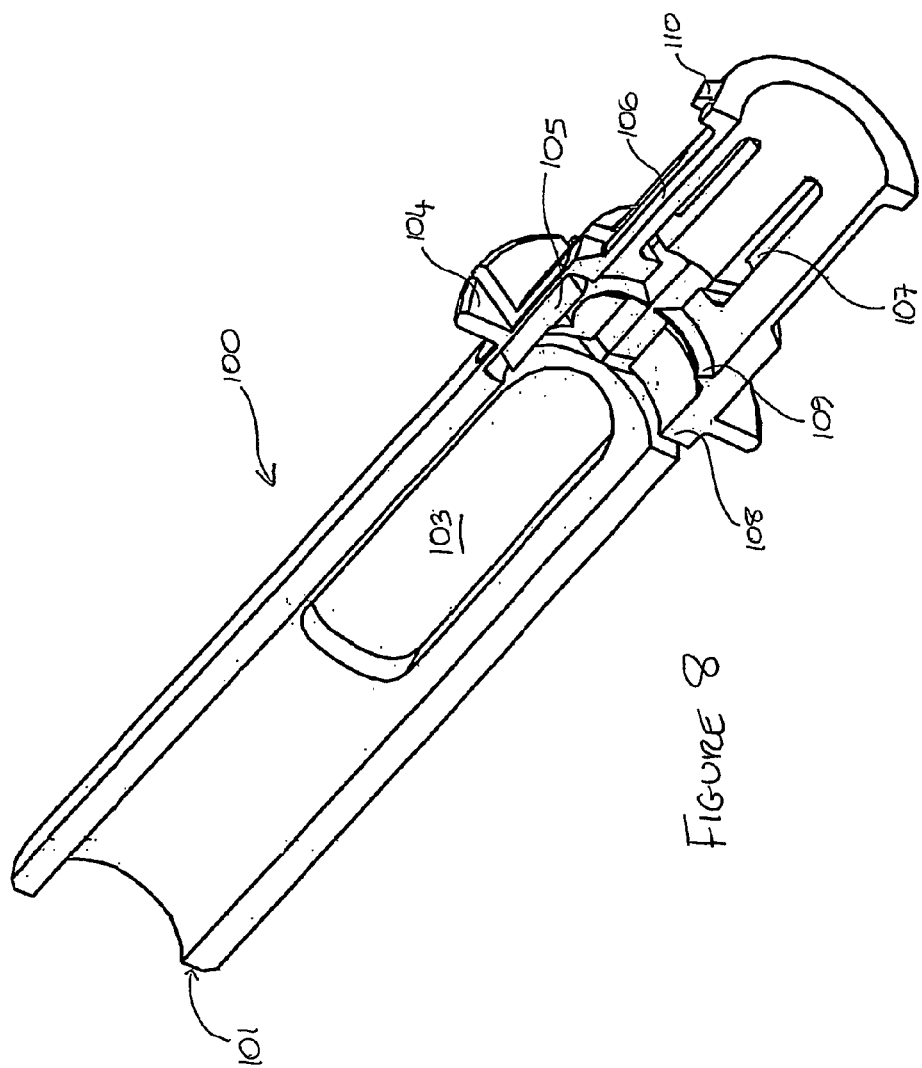
FIG. 8 is a cross-sectional view of the syringe holder of FIG. 7.

This problem is solved by the use of a syringe holder 100 as illustrated in FIGS. 7 and 8. The syringe holder 100 comprises an elongate rear portion 102 in which there are viewing windows 103 so that the medicament chamber in the barrel of a syringe held therein would be visible. There is a barrel seat 101 (equivalent to barrel seat 91 in the prior art device) at the rear end of the rear portion 102, but in practice this is not intended to abut the flange 90 of the syringe barrel (unlike in the prior art device).

The syringe holder also has an intermediate portion 105 of comparable diameter to the rear portion, and a front portion 106 of narrower diameter. The intermediate portion 105 is provided with a discontinuous annular flange 104. Together, the intermediate and front portions 105, 106 include radially-spaced slots 107 which define a plurality of radially flexible fingers 108. In the illustrated embodiment, there are three flexible fingers 108, but four or some other number of fingers may be provided. FIG. 22 shows an embodiment in which four flexible fingers 108 are provided on the syringe holder 100. The four fingers necessarily each are thinner than those in the three-finger embodiment. A typical example of a needle cover 17 is shown in FIG. 22 (illustrated without the rest of the syringe for simplicity). The needle cover has a slot 17A therein. If the syringe holder 100 is appropriately aligned with the needle cover of a syringe held therein, there is a possibility that one of the relatively thin flexible fingers 108 may undesirably snag or drop into slot 17A, possibly causing damage to the underlying needle that would not become apparent until an injection is delivered. This disadvantage can be overcome by ensuring that each of the flexible fingers 108 is preferably wider than the needle cover slot 17A, as illustrated by the three-finger embodiment of FIG. 7.

As shown in FIG. 8, gripping means 109 preferably in the form of a discontinuous annular inwardly-directed protrusion, are provided on the interior of the flexible fingers 108 in the intermediate section 105. Referring to FIG. 9, when a syringe is located within the syringe holder 100, the gripping means 109 abuts the front shoulder 92 of the barrel in order to define the axial position of the barrel with respect to the syringe holder.

The term "gripping means" is not limited to means which grip radially-inwardly onto the barrel, although in some embodiments they may do so. More important is the fact that the gripping means 109 (or equivalent) supports the syringe in a desired axial location and provides a reaction surface for the syringe so that the barrel will be held in compression during delivery of the medicament.

Figure 10:
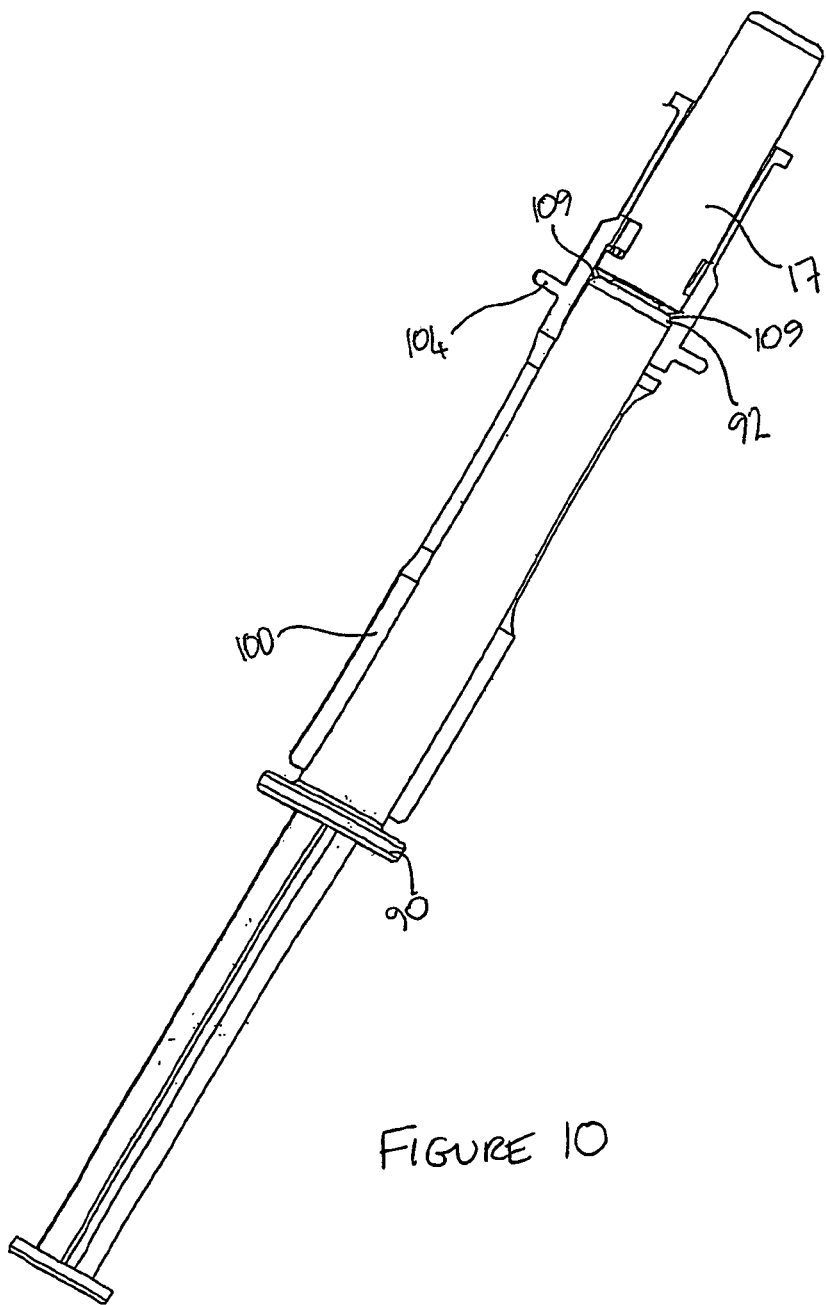
FIG. 10 is a cross-section view of the syringe holder of FIG. 7, showing a syringe, needle sheath and needle cover in place.
Figure 11:
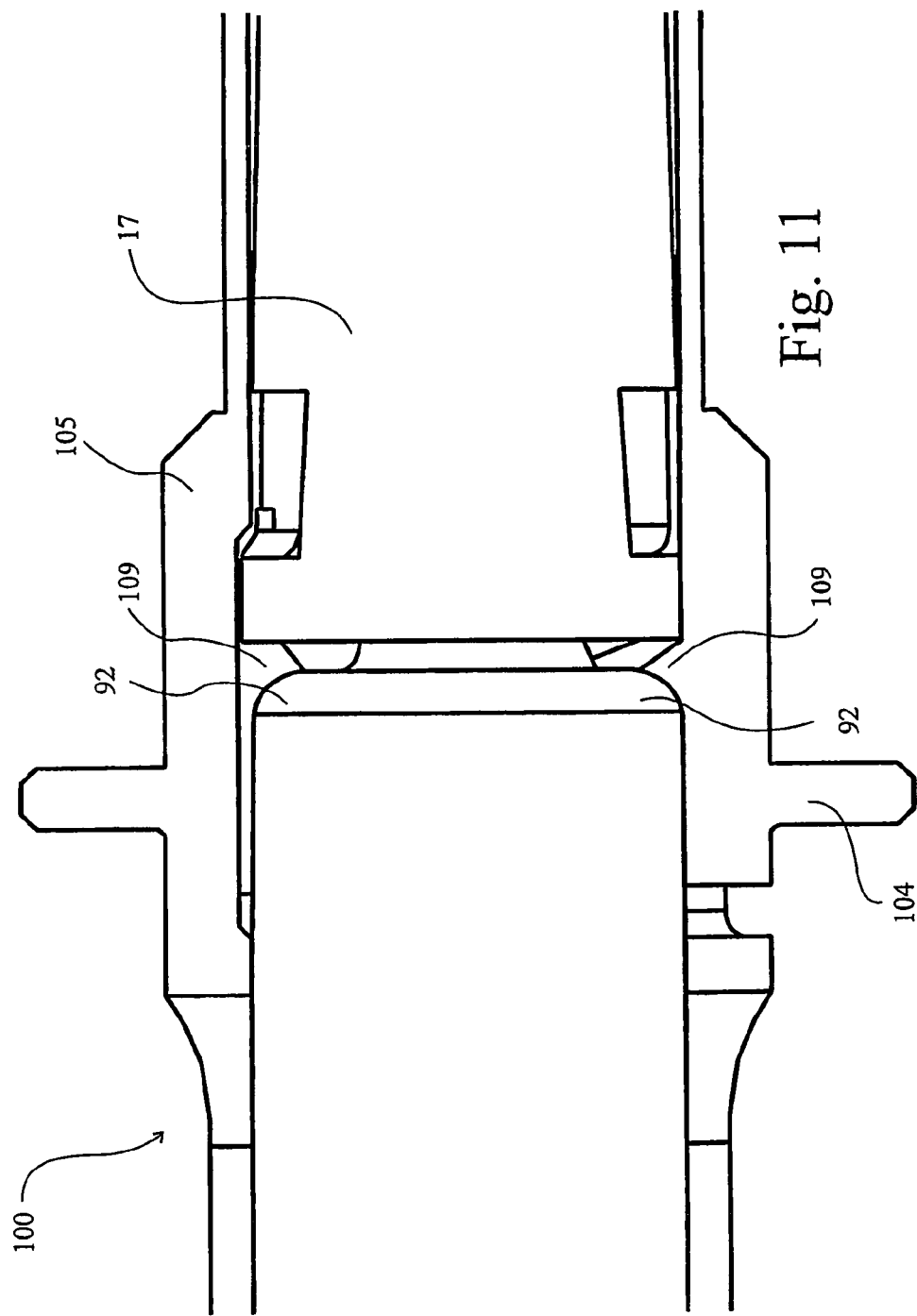
FIG. 11 shows detail, drawn to a larger scale, of the interface between the front of the glass syringe barrel and the syringe holder illustrated in FIG. 10.

As can be seen from FIGS. 10 and 11, the needle cover 17 has a greater diameter than the diameter normally available at the gripping means 109. In other words, the internal diameter between the gripping means 109 is smaller than the exterior diameter of the needle cover 17. However, as will be explained in more detail below, when the syringe is inserted into the syringe holder, as the needle cover 17 passes the gripping means 109, the flexible fingers 108 flex radially-outwardly to create sufficient diameter for the needle cover to pass the inwardly-protruding gripping means, without exerting excessive force on the needle therein, thus minimising the risk of damage to the needle. Once the needle cover has passed, the flexible fingers 108 spring back into their normal position (having smaller internal diameter than the exterior diameter of the needle cover) and the gripping means 109 locate at the front shoulder 92 of the barrel to provide the reaction surface against which the syringe will be held in compression during delivery of the medicament. In this position, the gripping means 109 are axially located between the needle cover and the front shoulder of the barrel.

The front portion 106 of the syringe support 100 is provided with a plurality of (preferably two) equispaced tags 110, whose purpose will be described later below.

The most straightforward way to assemble the syringe and injection device is in a three stage procedure, namely:
1. inserting the syringe into the syringe holder, until the gripping means 109 locate at the front shoulder 92 of the barrel;
2. inserting the syringe and syringe holder into the front part of the injection device;
3. assembling the front part to the rear part of the injection device.

Compared with the two-stage assembly procedure of the prior art device, the extra assembly stage is disadvantageous but initially seems necessary as it is not obvious how stages 1 and 2 could be readily combined so that the syringe holder can be supplied ready-assembled with the front part of the device. This is because, once assembled into the front part of the device, the flexible fingers 108 would be prevented from flexing radially outwardly by their necessarily close abutment with the front housing, thus preventing insertion of the syringe and needle cover.

Therefore, in a further embodiment of the invention, a modified front housing for the injection device is provided which enables a two-stage assembly procedure to be used.

Figure 12:
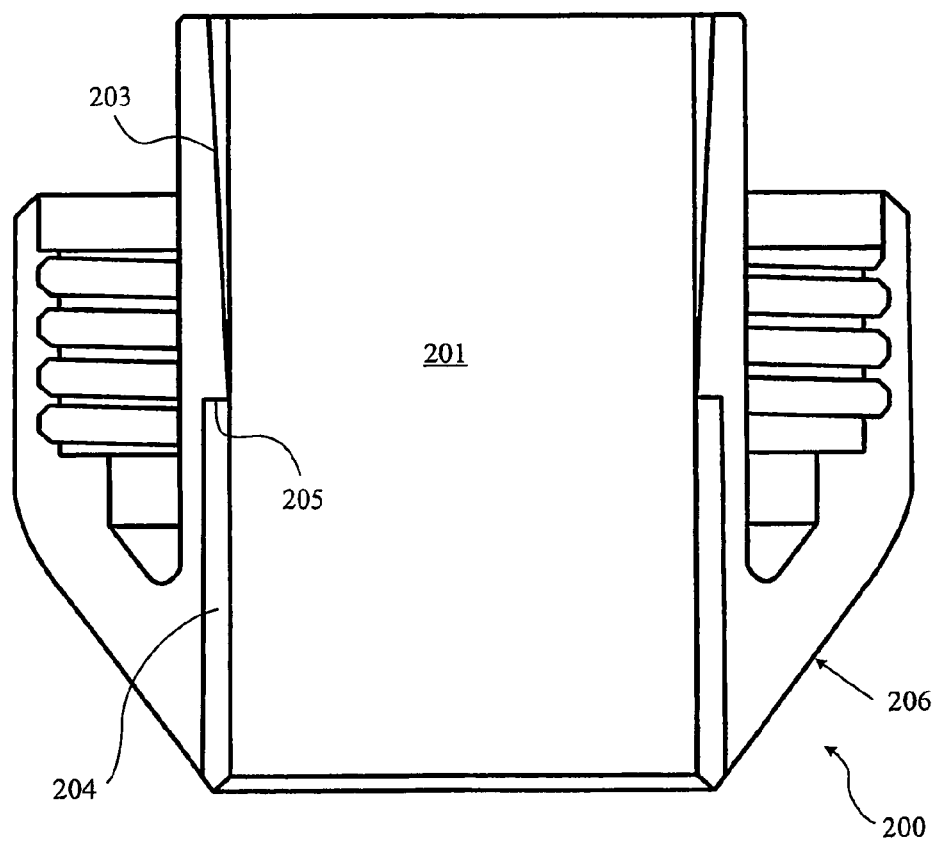
FIG. 12, drawn to a larger scale, is a cross-sectional view of the modified front housing.
Figure 13:
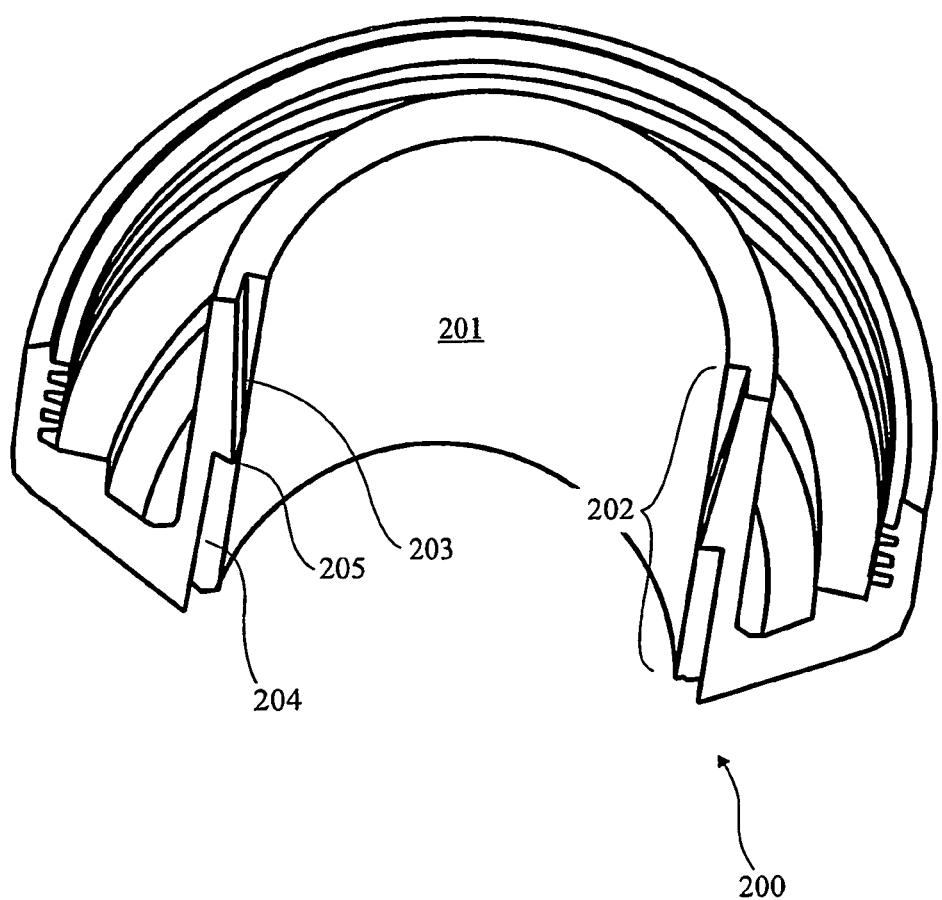
FIG. 13, drawn to a larger scale, is a perspective cross-sectional view of the front housing.

The modified front housing 200 (analogous to nozzle 11 in the prior art) is illustrated in FIG. 12. The front housing 200 has a bore 201, of sufficient diameter to allow passage therethrough of the needle 10, needle cover 17 and the front and intermediate portions 105, 106 of the syringe holder (but not the flange 104).

The interior surface of the bore 201 is provided with two (or more) equispaced longitudinal slots 202, each having a rear section 203 with a tapered surface providing a varying depth and a forward section 204 of substantially constant depth. The boundary between the forward and rear sections of each slot 202 is defined by a step 205.

The slots 202 are positioned so that they can be aligned with the tags 110 at the front portion of the syringe holder.

The slots 202 enable the syringe holder 100 to be assembled into the front housing 200 at a specific axial position (relative to the front housing) so that the flexible fingers 108 stand clear of the front housing instead of being surrounded therein.

The slots 202 also provide radial location for the syringe holder 100 as it is inserted therein.

Figure 14:
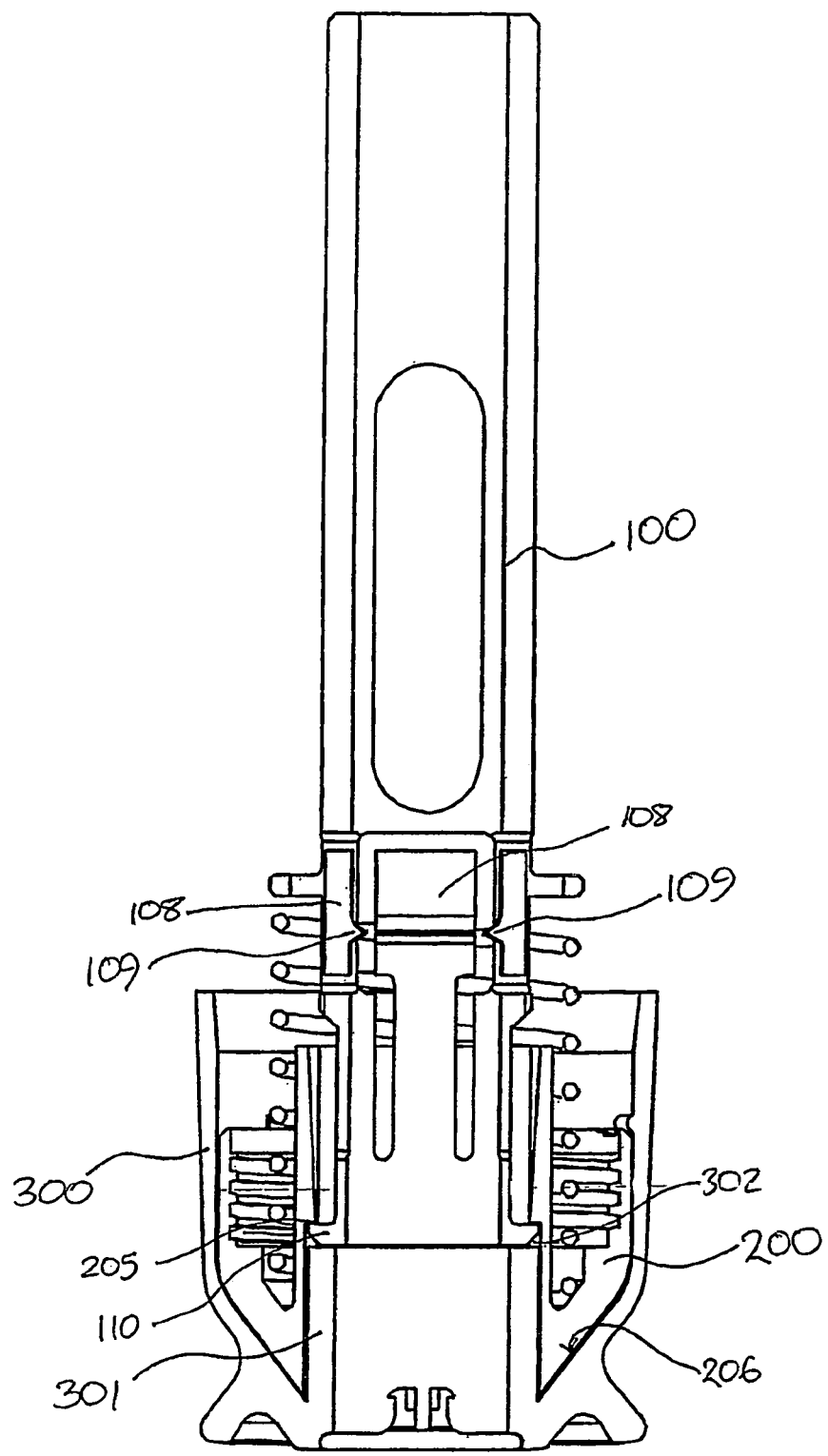
FIG. 14 is a cross-sectional view of the front housing, cap and syringe holder assembled together.

FIG. 14 shows a modified end cap 300 (analogous to end cap 15 in the prior art) designed for use with the modified front housing 200 and how the syringe holder 100 is inserted into the front housing 200. The front housing 200 is inserted into the end cap 300 so that its leading surface 206 abuts the interior of the end cap, so that no further forward movement of the front housing within the end cap is possible.

The close abutment of the end cap 300, front housing 200 and syringe holder 100 means that, if present, the needle cover 17 is retained securely in position such that the risk of the needle cover accidentally becoming loose or detached is minimised, thereby minimizing possible loss of integrity of the seal between the rubber needle sheath and the needle, which would otherwise compromise the sterility of the medicament contained within the syringe. The carefully engineered interaction between the components avoids the risk that during assembly, the syringe holder 100 might undesirably "snap" in between front end of the syringe barrel and the rear of the needle cover in such a way as to compromise the seal between the end of the needle and the needle sheath in which it is staked.

The end cap has an upstanding annulus 301 which protrudes into and is a close fit in the bore 201 of the front housing 200. The upstanding annulus 301 has two equispaced protrusions on the exterior surface thereof which locate in longitudinal slots 202 when the end cap and front housing are assembled together. Once assembled together, the upstanding annulus of the end cap and the step 205 together define a space 302 into which tags 110 on the syringe holder 100 can locate.

Figure 15:
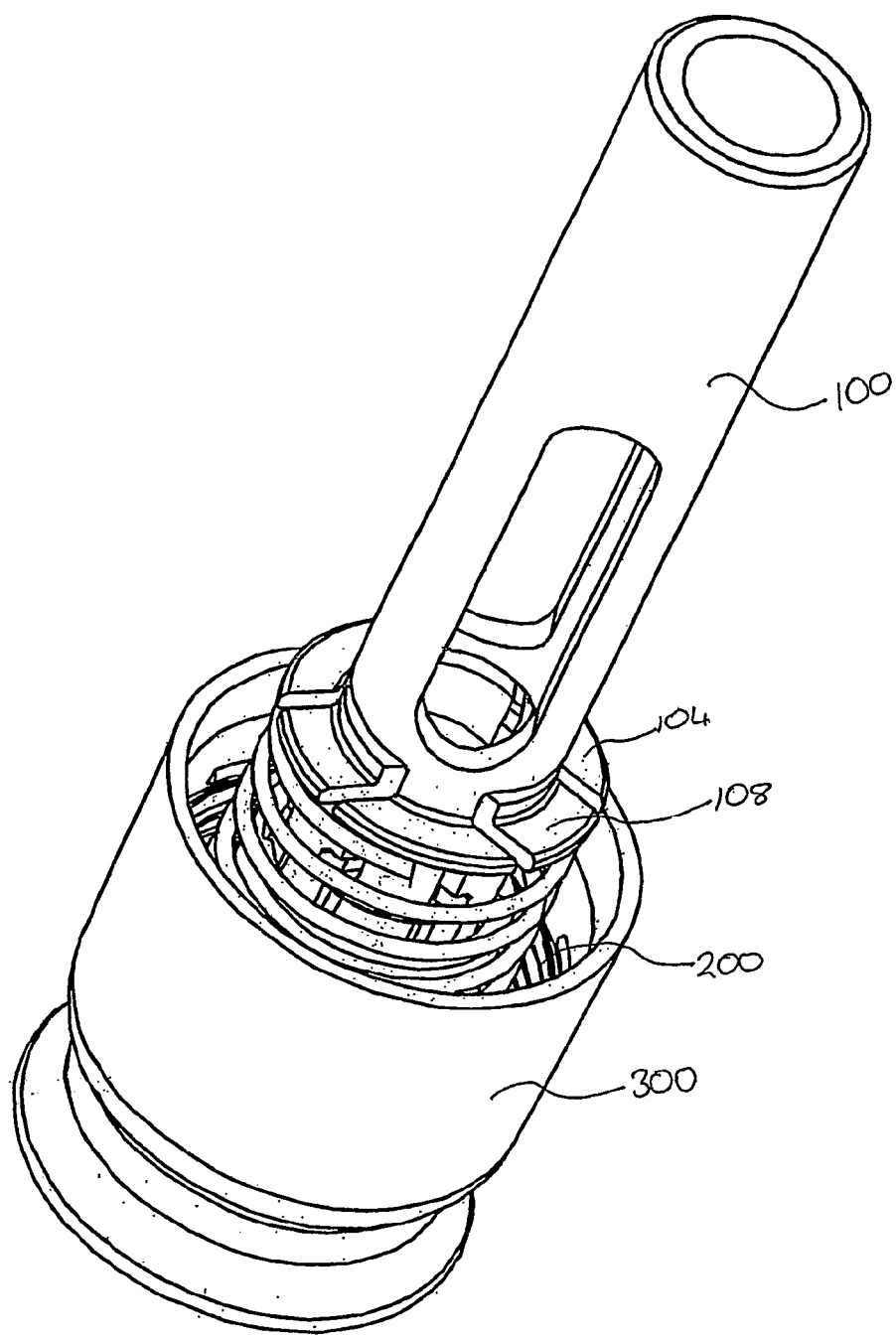
FIG. 15 is a perspective view of the front housing, cap and syringe holder assembled together.

In order to insert the syringe holder 100 into the front housing 200, the tags 110 are aligned with and pushed into the slots 202 until the tags 110 "click" over the step 205 and locate in the space 302. This is the position illustrated in FIGS. 14 and 15. Now the syringe holder 100 is suitably axially located such that the gripping means 109 and flexible fingers 108 are not constrained within the front housing 200 and end cap 300.

The front housing, end cap and syringe holder are supplied in this ready-assembled condition, together with the ready-assembled rear part of the injection device, for final assembly with a pre-filled syringe.

Figure 16:
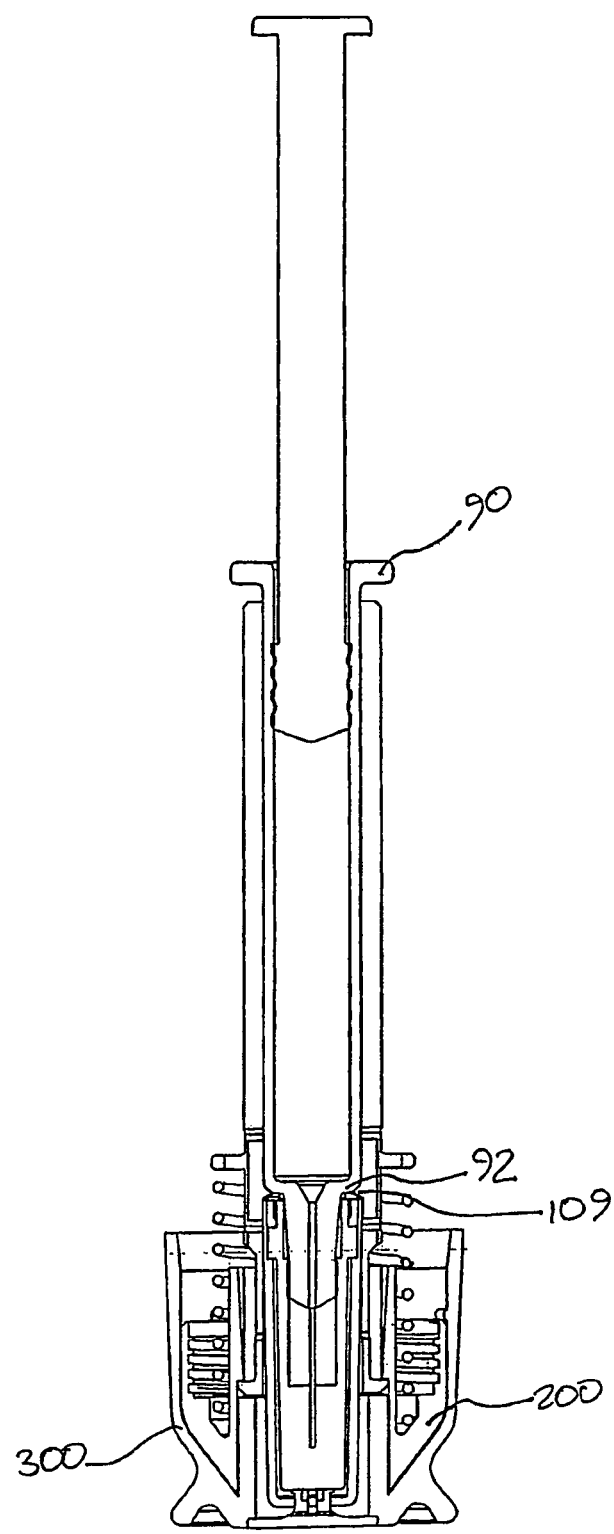
FIG. 16 is a cross-sectional view of the front housing, cap, syringe holder and syringe assembled together.

It is therefore a straightforward two-stage procedure to finally assemble the syringe into the device, namely:

1. inserting the syringe into the ready-assembled front housing, end cap and syringe holder until the gripping means 109 locate at the front shoulder 92 of the barrel (as shown in FIG. 16);
2. assembling the front part to the ready-assembled rear part of the injection device (not illustrated).

Figure 4:
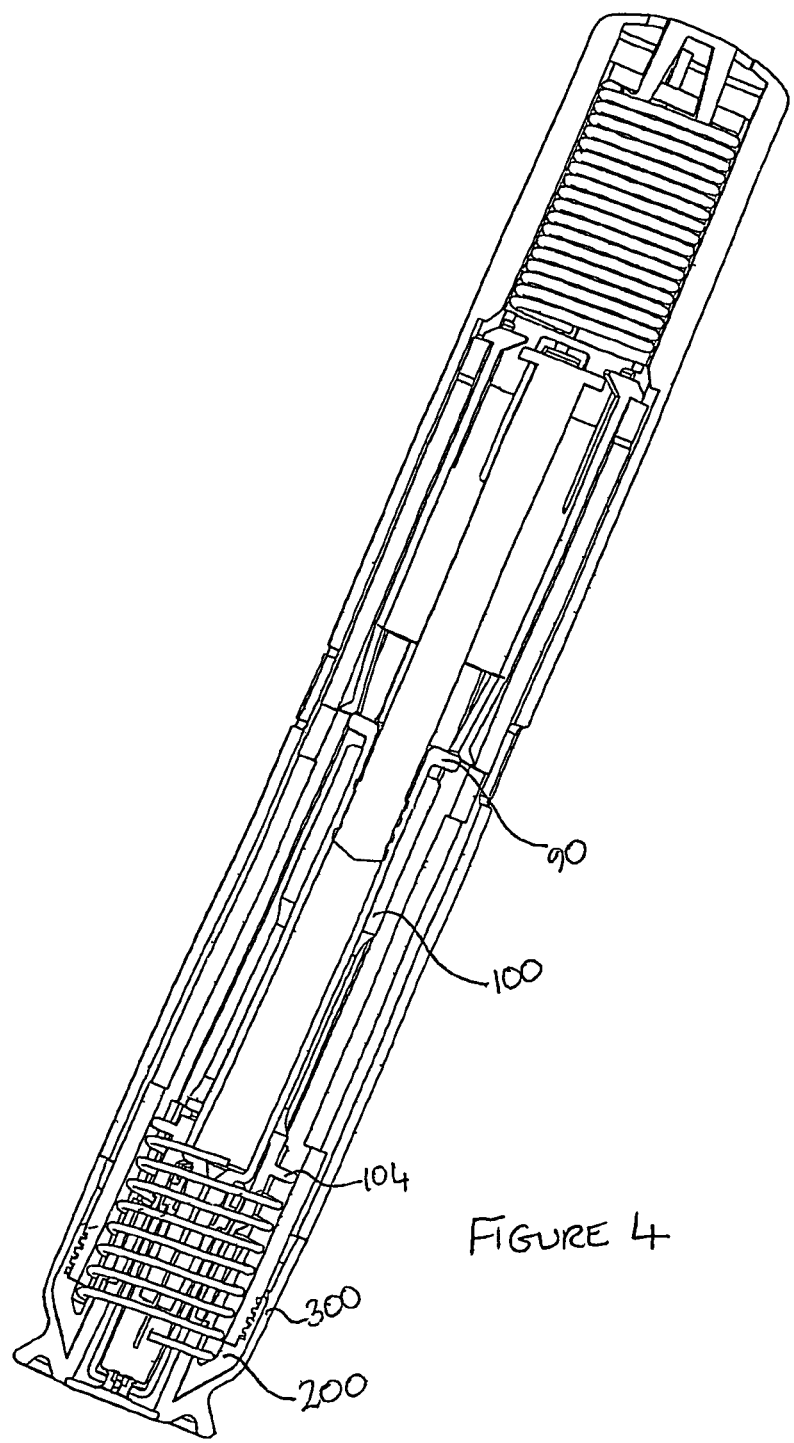
FIG. 4 is a perspective view of an injection device embodying one aspect of the present invention.
Figure 5:
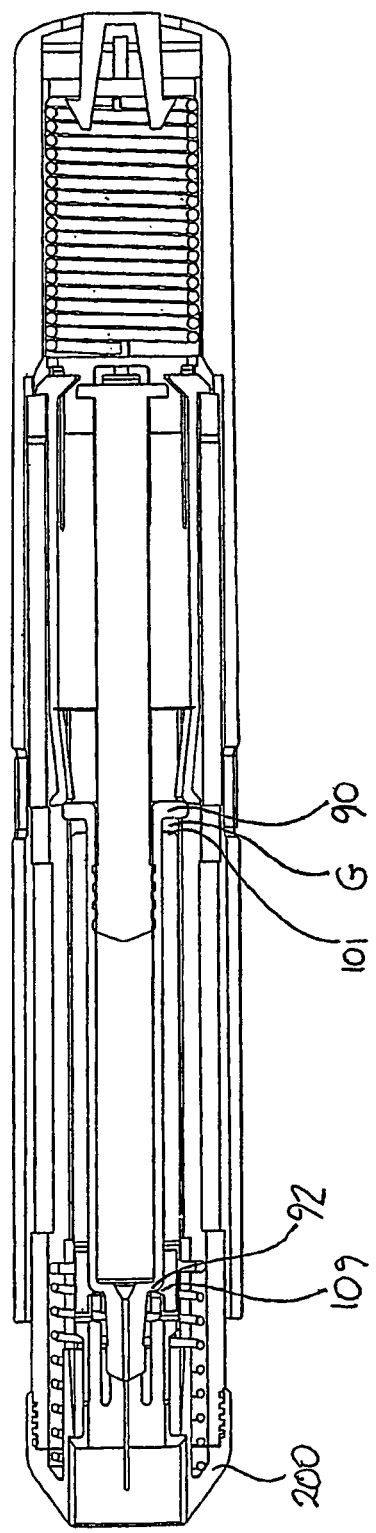
FIG. 5 is a plan view, partly in section of the FIG. 4 device, with the cap, needle cover and needle sheath removed, ready for actuation.
Figure 6:
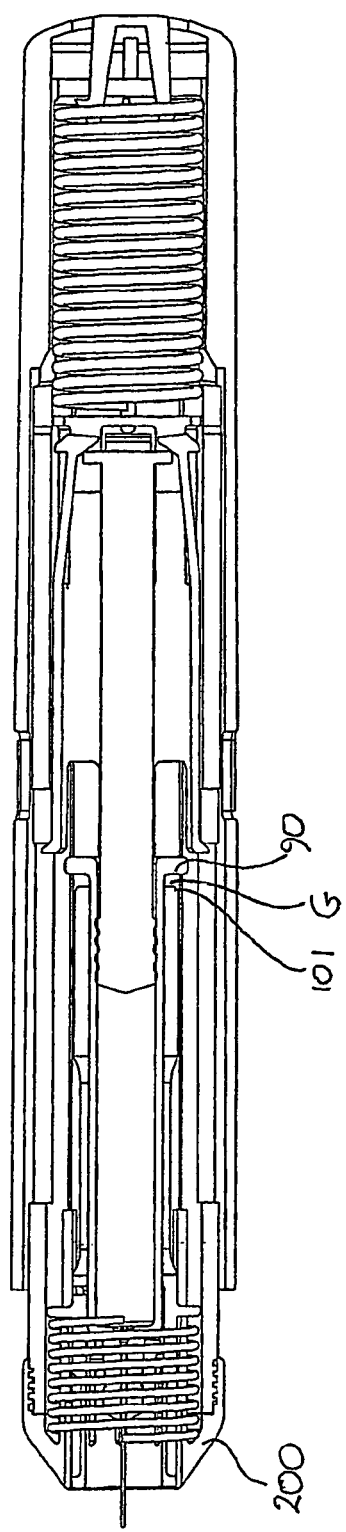
FIG. 6 is a plan view, partly in section of the FIG. 4 device, with the needle exposed, ready for the plunger to be depressed in order to deliver the medicament.

FIGS. 4-6 show the fully assembled injection device including syringe holder 100. With reference to FIG. 5, it can be seen that (unlike in the prior art device) the flange 90 of the barrel does not contact the barrel seat 101 of the syringe holder 100, there being a gap G therebetween. This is a result of the relative axial positions of the syringe holder and syringe being determined at the front end, by gripping means 109 and front shoulder 92 and means that undesirable tension is not applied to the glass barrel during delivery of the medicament.

An alternative embodiment of the syringe holder is illustrated in FIGS. 17-20. Where possible, the same reference numerals as were used in relation to FIGS. 8-9 are used to identify like components of the alternative embodiment. Note that FIGS. 17-20 show the front end of the device at the left side of the Figures, whereas FIGS. 8-9 show the front end of the device at the right side of the Figures.

Figure 17:
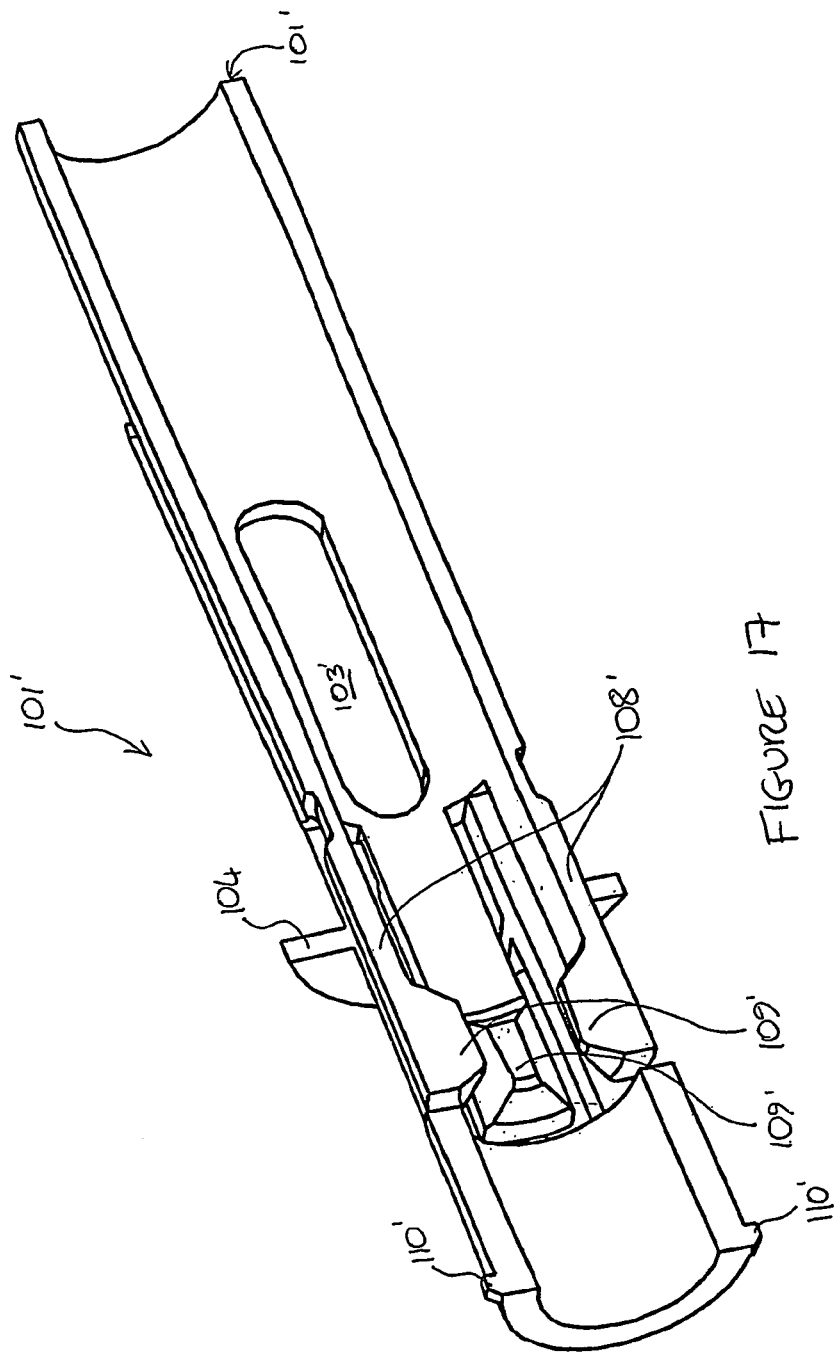
FIG. 17 is a cross-sectional view of an alternative embodiment of the syringe holder.
Figure 19:
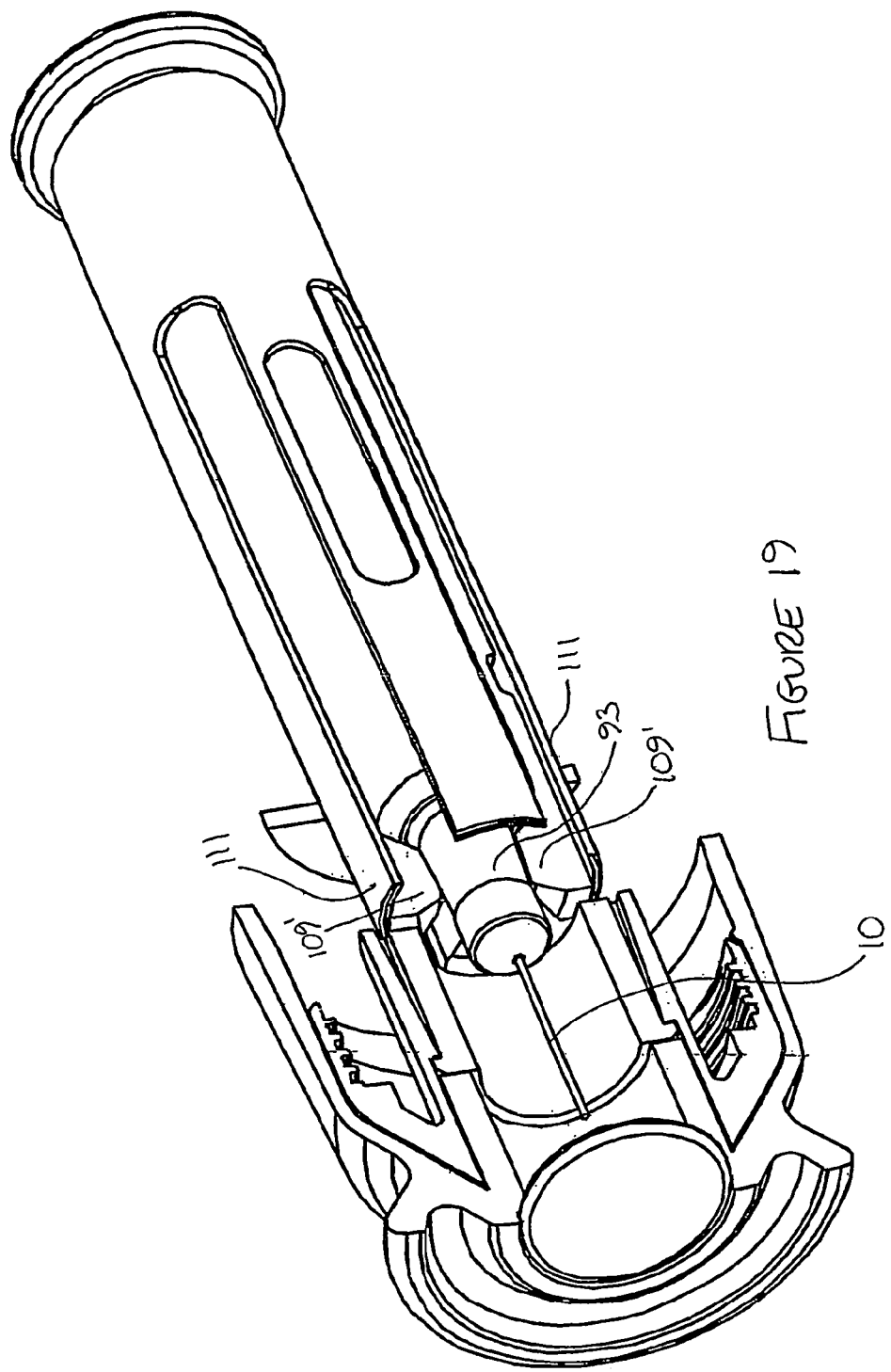
FIG. 19 shows the part-assembly of FIG. 18 with the needle cover removed.

In the FIG. 17 embodiment of the syringe holder 100', the radially-flexible fingers 108' have their free ends extending in the forward direction (compare with the radially-flexible fingers 108 in FIG. 8 which have their free ends extending in the rearward direction). The gripping means comprise inwardly-directed enlarged heads 109' at the end of the flexible fingers 108. As is best seen in FIG. 19, the enlarged heads 109' are capable of gripping the cone 93 at the front of the syringe barrel. The cone 93 is the region where the needle 10 is attached to the syringe barrel.

Figure 18:
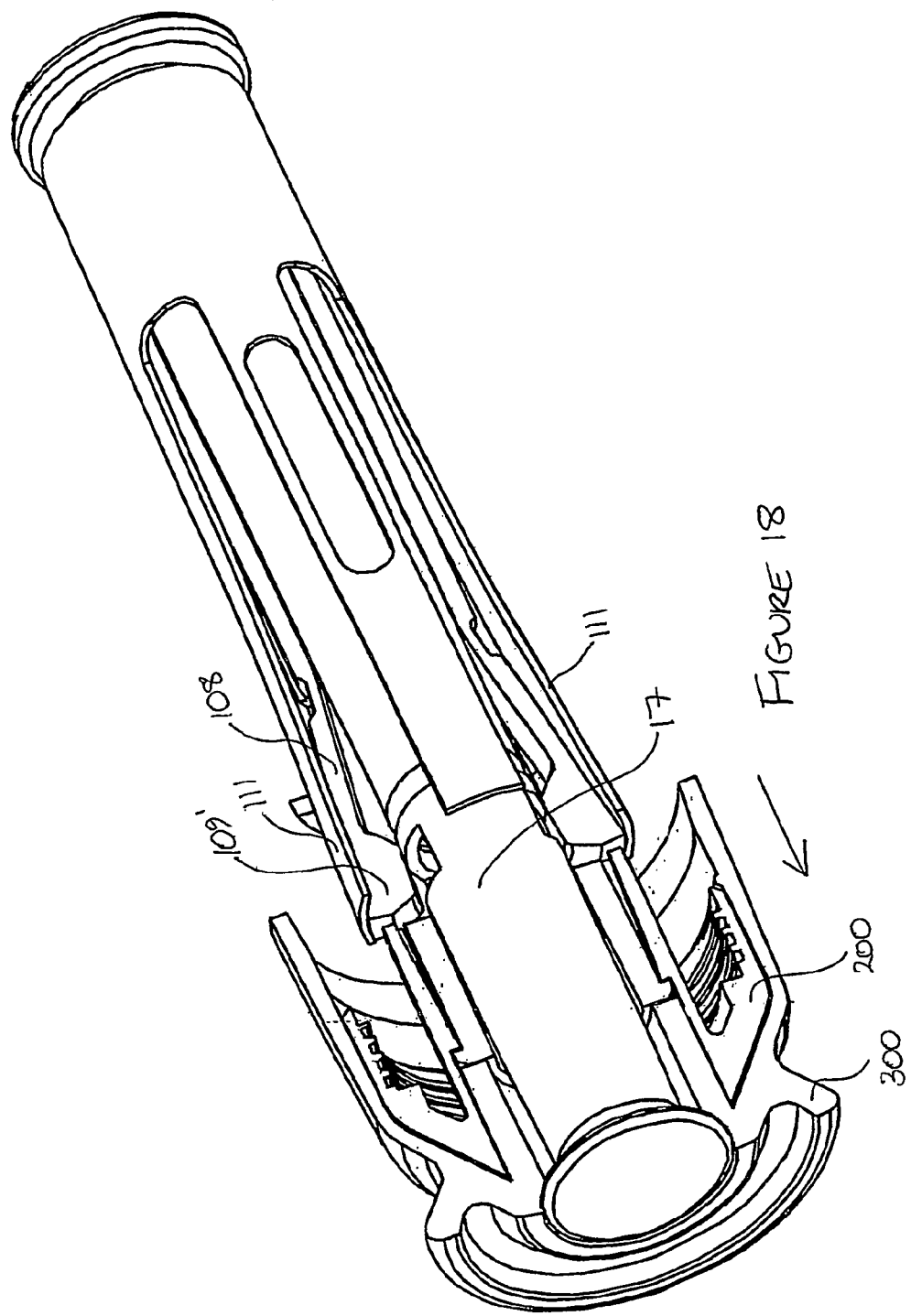
FIG. 18 is a part-assembly view showing the syringe holder of FIG. 17 together with its spring retainer, a syringe therein and the end cap and front housing.

As shown in FIG. 18, when a syringe is assembled with the syringe holder 100', the needle cover 17 (which is of comparable diameter to the syringe barrel) causes the flexible fingers 108' to flex radially-outwardly so that the enlarged heads 109' rest on the exterior of the needle cover 17.

When the end cap 300 and needle cover 17 are removed axially in the direction of the arrow in FIG. 18, the enlarged heads 109' should move radially-inwardly into contact with the cone 93 of the syringe so as to grip the front end of the barrel to provide the compressive force during injection. However, if the flexible fingers 108' are made from plastic and if the device is stored in the FIG. 18 configuration for many months before use (both of which are likely), it is possible that the fingers 108' will no longer automatically flex properly inwardly upon removal of the needle cover 17.

Figure 20:
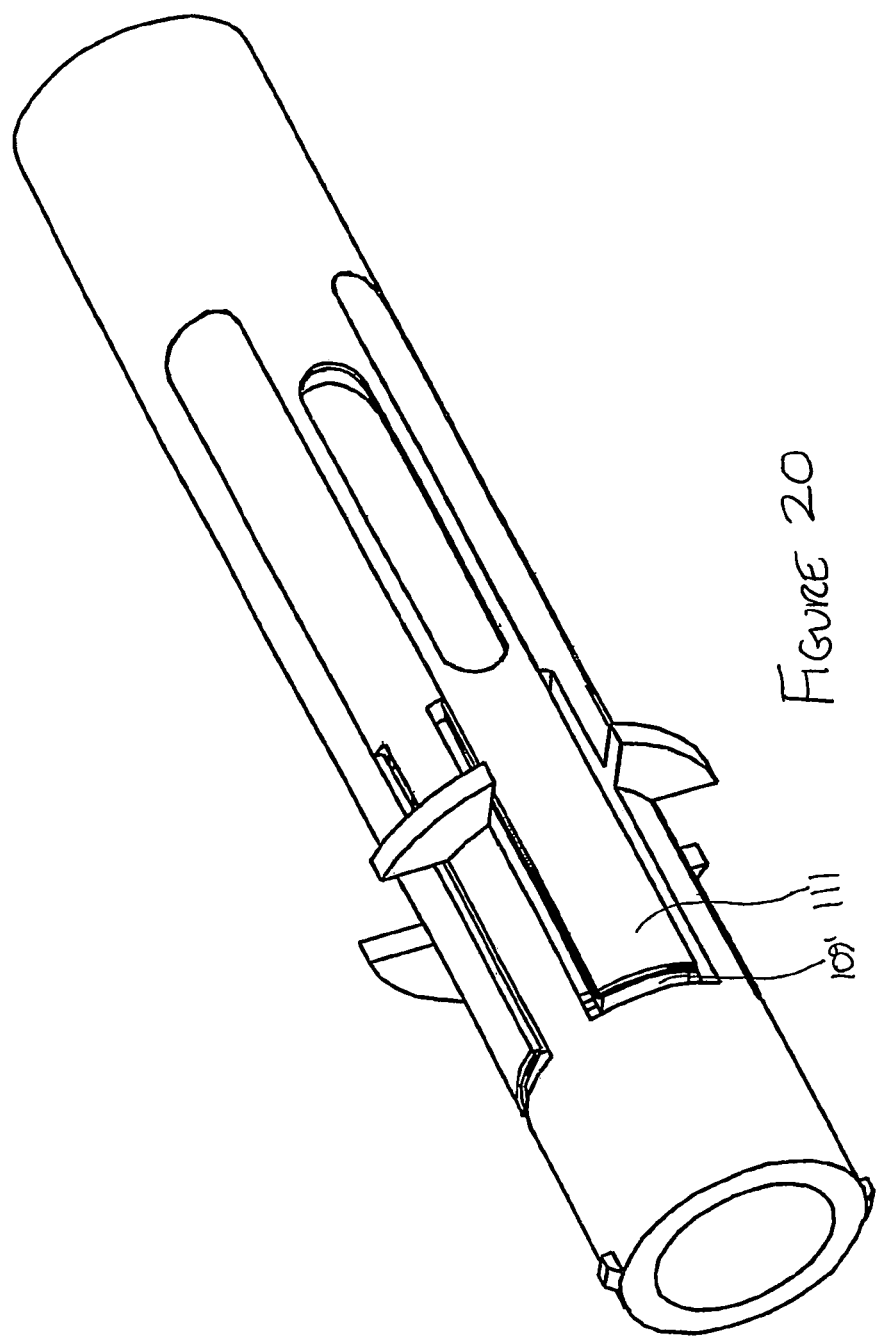
FIG. 20 is a perspective view of the syringe holder of FIG. 17 together with its spring retainer.

Therefore, a spring retainer 111 is provided. The spring retainer 111 is made from steel, other metal or other material which does not significantly lose its resilience over time. The spring retainer has elongate fingers which cooperate with the flexible fingers 108' so as to urge them radially-inwardly. Once the needle cover 17 has been removed, the spring retainer 111 urges the enlarged heads 109' into firm contact with the cone 93 of the syringe, even if the flexible fingers 108' are no longer capable of doing so. This position is illustrated in FIGS. 19 and 20.

Figure 21:
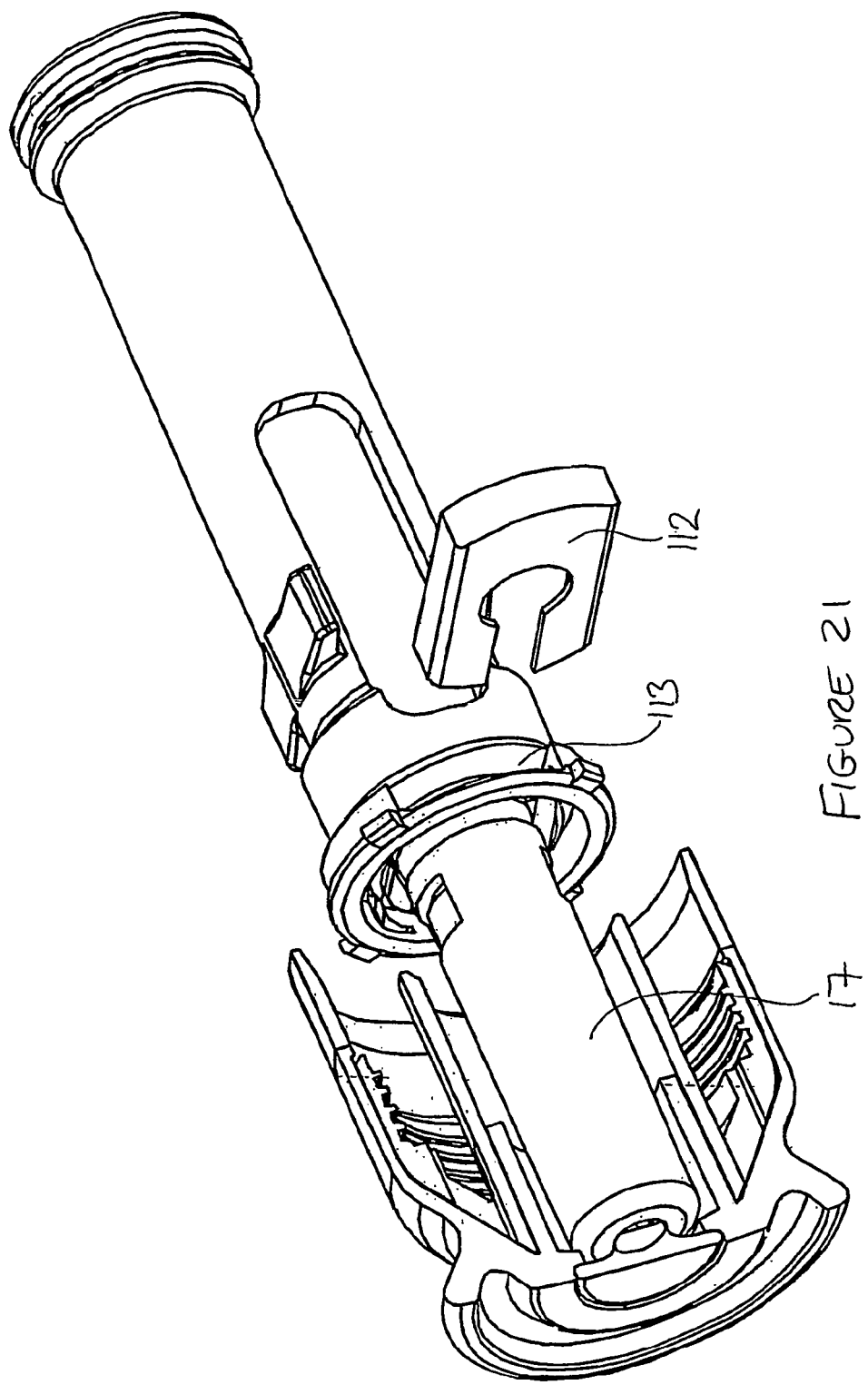
FIG. 21 is a perspective view of a syringe holder, end cap and front housing, showing an alternative means of retaining the gripping means against the syringe barrel.

As illustrated in FIG. 21, the gripping means (109 or 109') could alternatively be provided in the form of a clip 112, inserted axially into a slot 113 in the syringe holder so as to clip onto the front of the barrel.

Other means of providing a reaction surface for the front of the barrel so as to provide a compressive force during injection can be envisaged, for example a tapered elastomeric bush which could be snapped into place once the needle cover has passed during assembly. It may be possible to grip the frontmost part of the cone, where the needle enters the cone, rather than gripping the exterior thereof. Alternatively, other means for gripping the front shoulder of the barrel, or the exterior of the cone may be envisaged.

It is observed that the viewing windows 103, 103' in the syringe holder are apertures which create space through which glass fragments could move in the event of a breakage. If a breakage occurs, it is highly desirable to contain any glass fragments so as to minimise the risk of injury. Therefore, in an alternative embodiment (not illustrated), the apertures of the viewing windows are replaced by a solid but transparent or partially transparent material which still permits the user to view the interior of the syringe. Either the apertures 103, 103' can be "filled" with a transparent material so as to form a window in the more conventional sense of the word; alternatively, all of part of the syringe holder may be manufactured from transparent or partially transparent material.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:
1. An autoinjector configured to accommodate a syringe, comprising:
   a housing, including:
   one or more radially flexible fingers, said one or more radially flexible fingers defining at least one surface of a plurality of surfaces defining a substantially cylindrical cavity within said housing;
   a syringe support at a first end of the substantially cylindrical cavity, wherein said syringe support includes one or more inwardly-directed protrusions forming a reaction surface, wherein said inwardly-directed protrusions are on said one or more radially-flexible fingers, and wherein said one or more inwardly-directed protrusions form an axially-rearward facing cam surface where a sufficient forward axial force on said cam surface causes said one or more radially flexible fingers to flex radially outwardly;
   a syringe, including:
   a barrel for holding a volume of medicament,
   a needle at one end of the barrel in fluid communication with the medicament,
   a plunger axially-moveable in the barrel to a forwardmost position; and a needle sheath, the needle sheath sealing the forwardmost end of the needle to maintain sterility of the medicament within the barrel whereby, in use, the needle sheath must be removed from the needle immediately prior to actuating the autoinjector;

wherein said needle sheath substantially covers said needle to protect the needle from mechanical damage; and wherein the one or more inwardly-directed protrusions support the barrel at an axial location at or forward of the forwardmost position of the plunger.

2. The autoinjector of claim 1, wherein said needle sheath entirely covers said needle and seals against the syringe to maintain sterility of the external surface of the needle.

3. The autoinjector of claim 1, wherein said needle sheath comprises a solid elastomeric material into which the needle is spiked.

4. The autoinjector of claim 1, wherein said needle sheath is capable of being removed from the needle in an axially-forward direction immediately prior to actuating the autoinjector.

5. The autoinjector of claim 1, wherein said needle sheath is contained within a needle cover.

6. The autoinjector of claim 1, wherein said autoinjector is a single-use autoinjector.

7. The autoinjector of claim 1, further comprising an energy source for moving said plunger axially in the barrel to deliver an injection in less than 30 seconds.

8. The autoinjector of claim 1, wherein the syringe is axially moveable in said housing and is biased so that the needle is normally wholly inside said housing, wherein before injection the syringe is movable axially so as to move at least a part of said needle out of the housing and wherein after injection, the syringe is able to retract in order to retract said part of said needle into the housing.

9. The autoinjector of claim 1, wherein, in use, said reaction surface provides an axial compressive force to a front shoulder of the syringe barrel.

10. The autoinjector of claim 1, wherein, in use, said reaction surface provides an axial compressive force to a front cone of the syringe barrel.

11. The autoinjector of claim 1, wherein said inwardly-directed protrusions are on an end of said one or more radially-flexible fingers.

12. The autoinjector of claim 11, wherein said inwardly-directed protrusions comprise an inwardly-directed enlarged head on each radially-flexible finger.

13. The autoinjector of claim 11, further comprising a spring retainer for urging each radially-flexible finger inwardly.

14. The autoinjector of claim 13 wherein said spring retainer is made from steel.

15. The autoinjector of claim 11, wherein said radially-flexible fingers can flex sufficiently outwardly to allow a needle cover and a needle sheath of larger diameter than the internal diameter between said radially-flexible fingers to pass thereby during assembly of a syringe into said autoinjector.

16. The autoinjector of claim 15, wherein, when the device is fully assembled and ready for use, said inwardly-directed protrusions closely abut a needle cover and/or said needle sheath to reduce the risk of said needle sheath becoming loose or detached from a needle, potentially compromising the sterility of the needle.

17. The autoinjector of claim 1, wherein said housing includes a plurality of radially flexible fingers, wherein each radially flexible finger in said plurality of radially flexible fingers includes an inwardly-directed protrusion, wherein the internal diameter between said inwardly-directed protrusions is smaller than the diameter of the substantially cylindrical cavity within said housing.

18. The autoinjector of claim 17, wherein, when the autoinjector is fully assembled and ready for use, said inwardly-directed protrusions are axially located between a needle cover and the front shoulder of a syringe barrel.

19. The autoinjector of claim 1, wherein said substantially cylindrical cavity defined at least in part by said one or more radially flexible fingers of said housing has a diameter less than a diameter of a finger flange of a syringe barrel, and wherein the substantially cylindrical cavity is suitably sized to closely surround the syringe barrel in use.

20. The autoinjector of claim 19, wherein the finger flange of the syringe barrel does not contact the syringe support during delivery of the medicament.

21. The autoinjector of claim 1, wherein said syringe support is capable of supporting a syringe barrel at a specific axial location with respect thereto.

22. The autoinjector of claim 1, wherein said syringe support includes one or more viewing windows, to permit a user to view a barrel of a syringe supported therein.

23. The autoinjector of claim 22, wherein said one or more viewing windows comprise one or more apertures in the syringe support.

24. The autoinjector of claim 22, wherein said one or more viewing windows comprise a transparent or partially transparent part of the syringe support.

25. The autoinjector of claim 1, wherein said syringe support further comprises one or more tags at the front end thereof 26. The autoinjector of claim 25 further comprising:
a front housing having a bore therethrough, the interior surface of the bore being provided with one or more longitudinal slots, positioned so that said alignment tags can locate therein, when said front housing and syringe support are assembled together.

27. The autoinjector of claim 26, wherein each longitudinal slot comprises a rear section having a forwardly-increasing depth and a forward section having substantially constant depth.

28. The autoinjector of claim 27, wherein a boundary between the rear and forward sections is defined by a step.

29. The autoinjector of claim 28, further comprising:
an end cap having internal protrusions therein which protrude into the longitudinal slots in the bore of the front housing, when said end cap and said front housing are assembled together, so that a space is defined between said internal protrusions in the end cap and said step in the front housing.

30. The autoinjector of claim 29, wherein the tags of the syringe support locate into said defined space to determine an axial location of the syringe support with respect to said front housing.

31. The autoinjector of claim 30, wherein said radially-flexible fingers can flex sufficiently outwardly to allow a needle cover and a needle sheath of larger diameter than an internal diameter between said radially-flexible fingers to pass thereby during assembly of a syringe into said autoinjector, and wherein said axial location of the syringe support with respect to the front housing is such that said radially-flexible fingers are not confined within said front housing and are free to flex radially, when the front housing and syringe support are assembled together and before assembly of a rear part-assembly of the autoinjector thereto.

32. The autoinjector of claim 29, wherein, when assembled together, said end cap, front housing and syringe support substantially prevent damage to or movement of a needle cover and/or a needle sheath on a needle of a syringe mounted in the autoinjector.

33. The autoinjector of claim 26, wherein said syringe support includes a radially-extending flange, of greater diameter than an interior diameter of said front housing.

34. The autoinjector of claim 1, wherein the housing is an outer housing and at least part of the needle is axially moveable in and out of said outer housing but is biased to be normally wholly inside said housing, the autoinjector further comprising:
   an inner housing intermediate the outer housing and the barrel and plunger; and
   an energy source in communication with said inner housing,
   wherein the inner housing is moveable by the energy source between three positions, namely
      a first position in which the inner housing is in communication with the barrel such that, in use, the plunger and barrel are movable axially so as to move at least part of said needle out of the outer housing;
      a second position in which the inner housing is in communication with the plunger but not the barrel such that, in use, said plunger is movable axially into said barrel so as to expel medicament through the needle; and
      a third position in which the inner housing is in communication with neither the plunger nor the barrel such that, in use, the plunger and barrel are able to retract in order to retract the needle into the outer housing.

35. The autoinjector of claim 34, wherein said inner housing includes one or more flexible tags, biased radially inwardly by communication with said outer housing.

36. The autoinjector of claim 35, wherein one or more of said tags are situated at a rear end of the inner housing and are biased radially inwardly into communication with the plunger.

37. The autoinjector of claim 36, wherein each rear tag is moveable out of communication with the plunger when aligned with a corresponding recess in the outer housing.

38. The autoinjector of claim 35, wherein one or more of said tags are situated at a forward end of the inner housing and are biased radially inwardly into communication with the barrel.

39. The autoinjector of claim 38, wherein each forward tag is moveable out of communication with the barrel when aligned with a corresponding recess in the outer housing.

40. The autoinjector of claim 1, in which is mounted a syringe comprising
   a barrel for holding a volume of medicament,
   a needle at one end of the barrel in fluid communication with said medicament and
   a plunger axially-moveable in the barrel to a forwardmost position.

41. A method of assembling an autoinjector comprising the steps of:
   providing a first part-assembly comprising a front housing and a closely fitting end cap;
   providing a second part-assembly comprising a rear part of the autoinjector;
   providing a syringe comprising a barrel for holding a volume of medicament, a needle at one end of the barrel, a plunger axially-moveable in the barrel to a forwardmost position, and a needle cover covering the needle;
   providing a syringe support having a reaction surface for the syringe, wherein said syringe support includes one or more inwardly-directed protrusions forming said reaction surface, wherein said inwardly-directed protrusions are on one or more radially-flexible fingers, and wherein said one or more inwardly-directed protrusions further form an axially-rearward facing cam surface where a sufficient forward axial force on said cam surface causes said one or more radially flexible fingers to flex radially outwardly;
   inserting the syringe axially into the rear end of the syringe support so that said needle cover contacts said cam surface and causes said one or more radially flexible fingers to flex radially outwardly to allow said needle cover to pass until said syringe support supports the barrel of the syringe;
   inserting the front end of said syringe and syringe support into said first part-assembly;
   assembling said first part-assembly and second part-assembly together so that said syringe support supports the syringe at an axial location at or forward of the forwardmost position of the plunger, whereby in use said reaction surface provides an axial compressive force on said barrel when a forward axial force is applied to the plunger.

42. A method of assembling an autoinjector comprising the steps of:
   providing a first part-assembly comprising a syringe support, a front housing and a closely fitting end cap, wherein said syringe support includes one or more inwardly-directed protrusions forming a reaction surface, wherein said inwardly-directed protrusions are on one or more radially-flexible fingers, and wherein said one or more inwardly-directed protrusions further form an axially-rearward facing cam surface where a sufficient forward axial force on said cam surface causes said one or more radially flexible fingers to flex radially outwardly;
   providing a second part-assembly comprising a rear part of the autoinjector;
   providing a syringe comprising a barrel for holding a volume of medicament, a needle at one end of the barrel, a plunger axially-moveable in the barrel to a forwardmost position, and a needle cover covering the needle;
   inserting the syringe axially into the rear end of the first part-assembly so that said needle cover contacts said cam surface and causes said one or more radially flexible fingers to flex radially outwardly to allow said needle cover to pass until said syringe support supports the barrel of the syringe;
   assembling said first part-assembly and said second part-assembly together so that said syringe support supports the syringe at an axial location at or forward of the forwardmost position of the plunger, whereby in use said reaction surface provides an axial compressive force on said barrel when a forward axial force is applied to the plunger.

* * * * *